(12) United States Patent
Erickson et al.

(10) Patent No.: US 8,206,421 B2
(45) Date of Patent: Jun. 26, 2012

(54) METHODS AND DEVICES FOR INSERTION OF TETHERS THROUGH SUBCUTANEOUS SCREW HEADS

(75) Inventors: David R. Erickson, Memphis, TN (US); Jeffrey Zhang, Collierville, TN (US); John D. Pond, Germantown, TN (US); Robert G. Carson, Memphis, TN (US); Randall N. Allard, Germantown, TN (US); Robert H. Dyer, Barlett, TN (US)

(73) Assignee: Warsaw Othropedic, Inc., Warsaw, IN (US)

( * ) Notice: Subject to any disclaimer, the term of this patent is extended or adjusted under 35 U.S.C. 154(b) by 885 days.

(21) Appl. No.: 12/121,340

(22) Filed: May 15, 2008

(65) Prior Publication Data

US 2009/0287255 A1 Nov. 19, 2009

(51) Int. Cl.
A61B 17/88 (2006.01)
(52) U.S. Cl. .......................... 606/279; 606/263
(58) Field of Classification Search .................. 606/279, 606/263, 74, 86 R, 99, 103, 104, 86 A, 914, 606/916, 300–321, 228–233
See application file for complete search history.

(56) References Cited

U.S. PATENT DOCUMENTS

| 6,059,786 | A * | 5/2000 | Jackson .................... 606/916 |
| 6,436,099 | B1 | 8/2002 | Drewry et al. |
| 6,607,530 | B1 | 8/2003 | Carl et al. |
| 6,821,277 | B2 | 11/2004 | Teitelbaum |
| 6,923,811 | B1 | 8/2005 | Carl et al. |
| 7,008,422 | B2 | 3/2006 | Foley et al. |
| 7,008,424 | B2 | 3/2006 | Teitelbaum |
| 7,011,660 | B2 | 3/2006 | Sherman et al. |
| 7,018,379 | B2 | 3/2006 | Drewry et al. |
| 7,179,261 | B2 | 2/2007 | Sicvol et al. |
| 7,188,626 | B2 | 3/2007 | Foley et al. |
| 7,303,562 | B2 | 12/2007 | Cavagna et al. |
| 2002/0007184 | A1 | 1/2002 | Ogilvie et al. |
| 2002/0023241 | A1 | 2/2002 | Kabune et al. |
| 2002/0082598 | A1 | 6/2002 | Teitelbaum |
| 2002/0161368 | A1 | 10/2002 | Foley et al. |
| 2003/0023241 | A1 | 1/2003 | Drewry et al. |
| 2003/0060826 | A1 | 3/2003 | Foley et al. |
| 2003/0083657 | A1 | 5/2003 | Drewry et al. |
| 2003/0229347 | A1 | 12/2003 | Sherman et al. |
| 2004/0006341 | A1* | 1/2004 | Shaolian et al. ................ 606/61 |
| 2004/0034351 | A1 | 2/2004 | Sherman et al. |
| 2004/0059338 | A1 | 3/2004 | Ebner |
| 2004/0172025 | A1 | 9/2004 | Drewry et al. |
| 2004/0215191 | A1 | 10/2004 | Kitchen |
| 2005/0021031 | A1 | 1/2005 | Foley et al. |
| 2005/0038432 | A1 | 2/2005 | Shaolian et al. |
| 2005/0171540 | A1 | 8/2005 | Lim et al. |

(Continued)

*Primary Examiner* — Eduardo C Robert
*Assistant Examiner* — Michelle C Eckman

(57) ABSTRACT

A method of securing vertebrae includes inserting a first pedicle screw into a first pedicle of a first vertebra. The first pedicle screw includes a first channel running perpendicular to a first central axis of the first pedicle screw. The first pedicle screw has a first engagement structure. The method further includes inserting a second pedicle screw into a second pedicle of a second vertebra. The second pedicle screw includes a second channel running perpendicular to a second central axis of the second pedicle screw. The second pedicle screw has a second engagement structure. The method also includes inserting a guidewire through the first and second channels, threading a tether attached to an end of the guidewire through the first and second channels, securing the tether to the first pedicle screw, applying tension to the tether, and securing the tether to the second pedicle screw.

8 Claims, 19 Drawing Sheets

U.S. PATENT DOCUMENTS

| | | |
|---|---|---|
| 2005/0203514 A1 | 9/2005 | Jahng et al. |
| 2005/0277934 A1* | 12/2005 | Vardiman .................. 606/61 |
| 2006/0023241 A1 | 2/2006 | Funakami |
| 2006/0111714 A1 | 5/2006 | Foley |
| 2006/0122597 A1 | 6/2006 | Jones et al. |
| 2006/0122608 A1* | 6/2006 | Fallin et al. ................ 606/72 |
| 2006/0195087 A1 | 8/2006 | Scher et al. |
| 2006/0195088 A1 | 8/2006 | Sacher et al. |
| 2006/0200135 A1 | 9/2006 | Sherman et al. |
| 2006/0217713 A1 | 9/2006 | Serhan et al. |
| 2006/0217714 A1 | 9/2006 | Serhan et al. |
| 2006/0217715 A1 | 9/2006 | Serhan et al. |
| 2006/0229614 A1 | 10/2006 | Foley et al. |
| 2006/0264942 A1 | 11/2006 | Lim et al. |
| 2007/0005063 A1 | 1/2007 | Bruneau et al. |
| 2007/0016194 A1 | 1/2007 | Shaolian et al. |
| 2007/0049931 A1 | 3/2007 | Justis et al. |
| 2007/0162007 A1 | 7/2007 | Shoham |
| 2007/0299444 A1* | 12/2007 | DiPoto et al. .................. 606/61 |
| 2008/0114403 A1* | 5/2008 | Kuester et al. ............... 606/308 |
| 2008/0312704 A1* | 12/2008 | Hestad et al. .............. 606/86 A |
| 2009/0171391 A1* | 7/2009 | Hutton et al. ................ 606/246 |

* cited by examiner

METHODS AND DEVICES FOR INSERTION OF TETHERS THROUGH SUBCUTANEOUS SCREW HEADS

FIELD OF THE DISCLOSURE

The present disclosure relates generally to orthopedics and orthopedic surgery. More specifically, the present disclosure relates to methods and devices for insertion of tethers through subcutaneous screw heads.

BACKGROUND

In human anatomy, the spine is a generally flexible column that can take tensile and compressive loads. The spine also allows bending motion and provides a place of attachment for tendons, muscles and ligaments. Generally, the spine is divided into four sections: the cervical spine, the thoracic or dorsal spine, the lumbar spine, and the pelvic spine. The pelvic spine generally includes the sacrum and the coccyx. The sections of the spine are made up of individual bones called vertebrae. Also, the vertebrae are separated by intervertebral discs, which are situated between adjacent vertebrae.

The intervertebral discs function as shock absorbers and as joints. Further, the intervertebral discs can absorb the compressive and tensile loads to which the spinal column may be subjected. At the same time, the intervertebral discs can allow adjacent vertebral bodies to move relative to each other a limited amount, particularly during bending or flexure of the spine. Thus, the intervertebral discs are under constant muscular and gravitational pressure and generally, the intervertebral discs are the first parts of the lumbar spine to show signs of deterioration.

Facet joint degeneration is also common because the facet joints are in almost constant motion with the spine. In fact, facet joint degeneration and disc degeneration frequently occur together. Generally, although one may be the primary problem while the other is a secondary problem resulting from the altered mechanics of the spine, by the time surgical options are considered, both facet joint degeneration and disc degeneration typically have occurred. For example, the altered mechanics of the facet joints and the intervertebral disc may cause spinal stenosis, degenerative spondylolisthesis, and degenerative scoliosis.

In addition to degeneration, the spine may be injured through traumatic events, such as automobile accidents, falls, or over exertion. Such spinal injuries may lead to surgery to repair broken vertebra or to fortify the spine.

However, such surgeries tend to utilize large incisions and extensive tissue retraction. In many typical surgeries, muscle and ligament tissues are retracted or are surgically detached during the surgery and reattached afterward. As a result, such surgeries lead to long recovery time, patient discomfort, an increased risk of infection, and high expense.

As such, an improved apparatus and method for performing spinal surgeries would be desirable.

BRIEF DESCRIPTION OF THE DRAWINGS

The present disclosure may be better understood, and its numerous features and advantages made apparent to those skilled in the art by referencing the accompanying drawings.

The use of the same reference symbols in different drawings indicates similar or identical items.

DETAILED DESCRIPTION

In a particular embodiment, a surgical method may include implanting a surgical assembly that includes a set of subcutaneous screws and a tether extending between the subcutaneous screws. In an example, the subcutaneous screws are pedicle screws that are inserted into the pedicles of vertebrae. The subcutaneous screws include a channel to receive a tether and include an engagement structure to receive a set screw to secure the tether. In an exemplary method, a guidewire is inserted through the channels of the set of subcutaneous screws, a tether attached to the guidewire is threaded through the channels, and the set screws secure the tether after tension is applied to the tether. In another exemplary method, a trocar, a sheath, or a cannulated rod are used to assist with threading the tether through the channels of the set of subcutaneous screws. Optionally, the subcutaneous screws may be accessed percutaneously with the use of a percutaneous rod coupled to the subcutaneous screw.

Description of Relevant Anatomy

Figure 1:
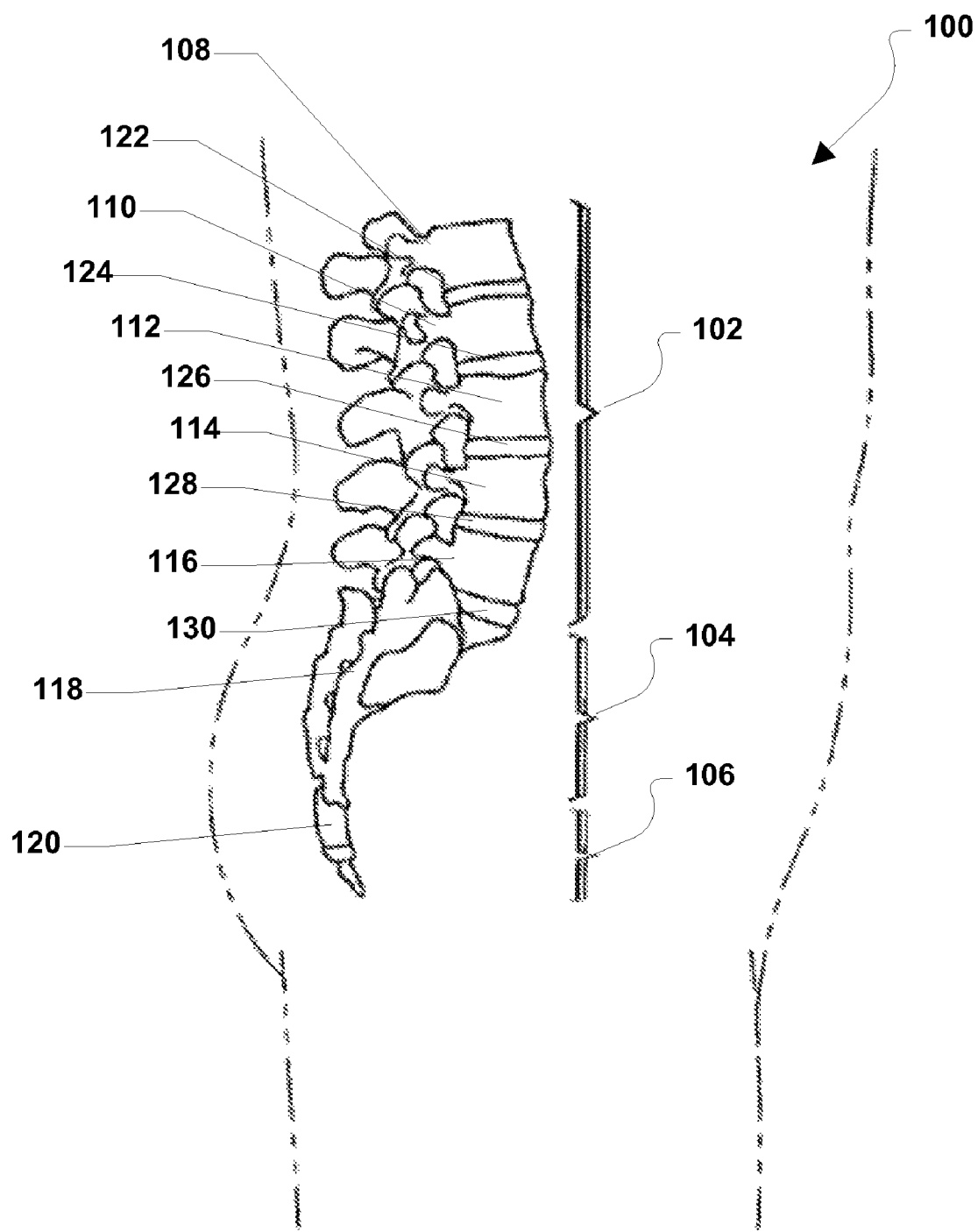
FIG. 1 includes a lateral view illustration of a portion of a vertebral column.

Referring initially to FIG. 1, a portion of a vertebral column, designated 100, is illustrated. As depicted, the vertebral column 100 includes a lumbar region 102, a sacral region 104, and a coccygeal region 106. The vertebral column 100 also includes a cervical region and a thoracic region. For clarity and ease of discussion, the cervical region and the thoracic region are not illustrated.

As illustrated in FIG. 1, the lumbar region 102 includes a first lumbar vertebra 108, a second lumbar vertebra 110, a third lumbar vertebra 112, a fourth lumbar vertebra 114, and a fifth lumbar vertebra 116. The sacral region 104 includes a sacrum 118. Further, the coccygeal region 106 includes a coccyx 120.

As depicted in FIG. 1, a first intervertebral lumbar disc 122 is disposed between the first lumbar vertebra 108 and the second lumbar vertebra 110. A second intervertebral lumbar disc 124 is disposed between the second lumbar vertebra 110 and the third lumbar vertebra 112. A third intervertebral lumbar disc 126 is disposed between the third lumbar vertebra 112 and the fourth lumbar vertebra 114. Further, a fourth intervertebral lumbar disc 128 is disposed between the fourth lumbar vertebra 114 and the fifth lumbar vertebra 116. Additionally, a fifth intervertebral lumbar disc 130 is disposed between the fifth lumbar vertebra 116 and the sacrum 118.

In a particular embodiment, if one of the intervertebral lumbar discs 122, 124, 126, 128, 130 is diseased, degenerated, damaged, or otherwise in need of repair, treatment of that intervertebral lumbar disc 122, 124, 126, 128, 130 can be effected in accordance with one or more of the embodiments described herein. In another embodiment, misalignment of two or more vertebra (108, 110, 112, 114, or 116) or damage to the facet joints may be treated in accordance with one or more of the embodiments described herein.

Figure 2:
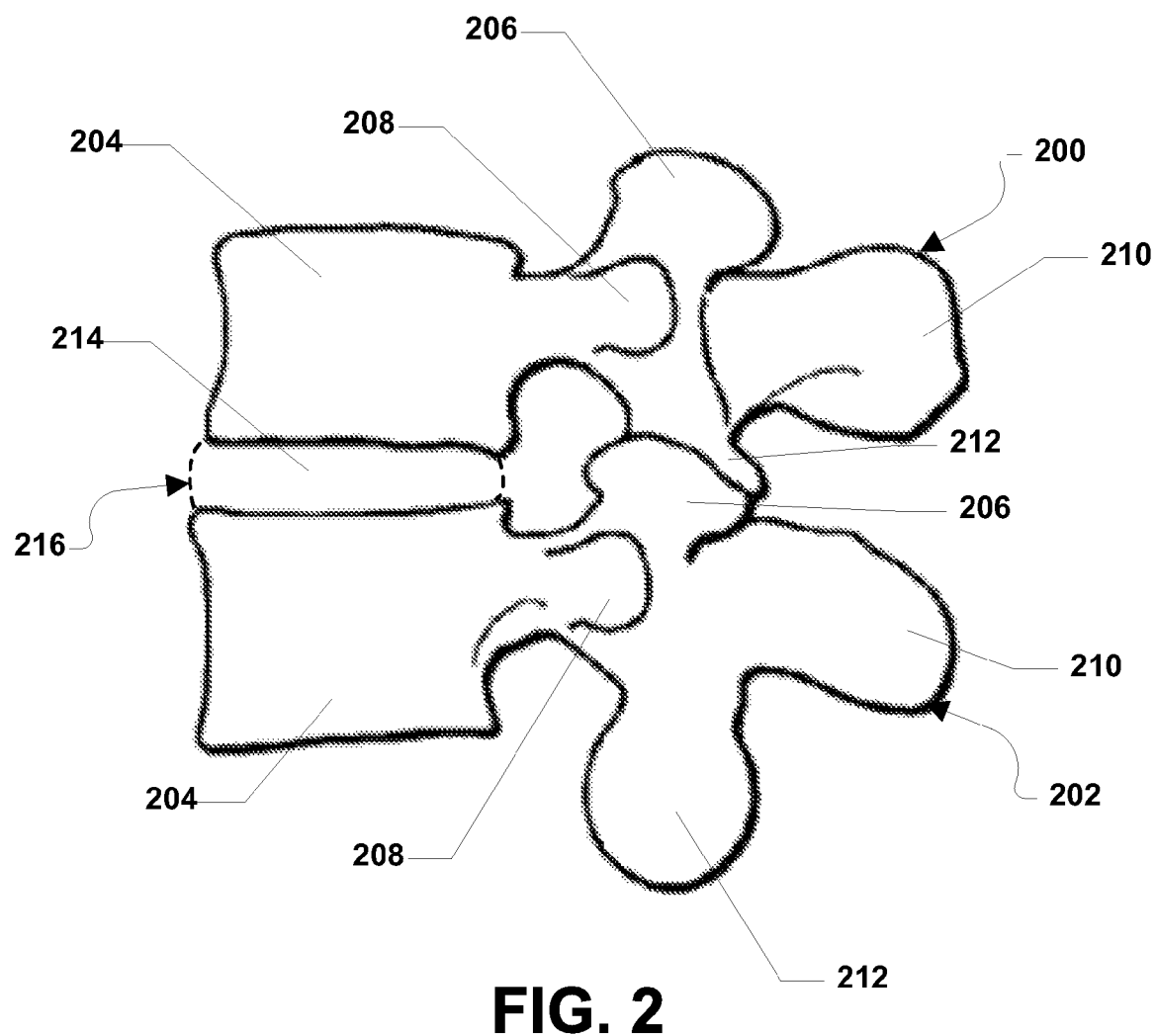
FIG. 2 includes a lateral view illustration of a pair of adjacent vertebrae.

FIG. 2 depicts a detailed lateral view of two adjacent vertebrae, e.g., two of the lumbar vertebra 108, 110, 112, 114, 116 illustrated in FIG. 1. FIG. 2 illustrates a superior vertebra 200 and an inferior vertebra 202. As illustrated, each vertebra 200, 202 includes a vertebral body 204, a superior articular process 206, a transverse process 208, a spinous process 210 and an inferior articular process 212. FIG. 2 further depicts an intervertebral disc 216 between the superior vertebra 200 and the inferior vertebra 202.

Figure 3:
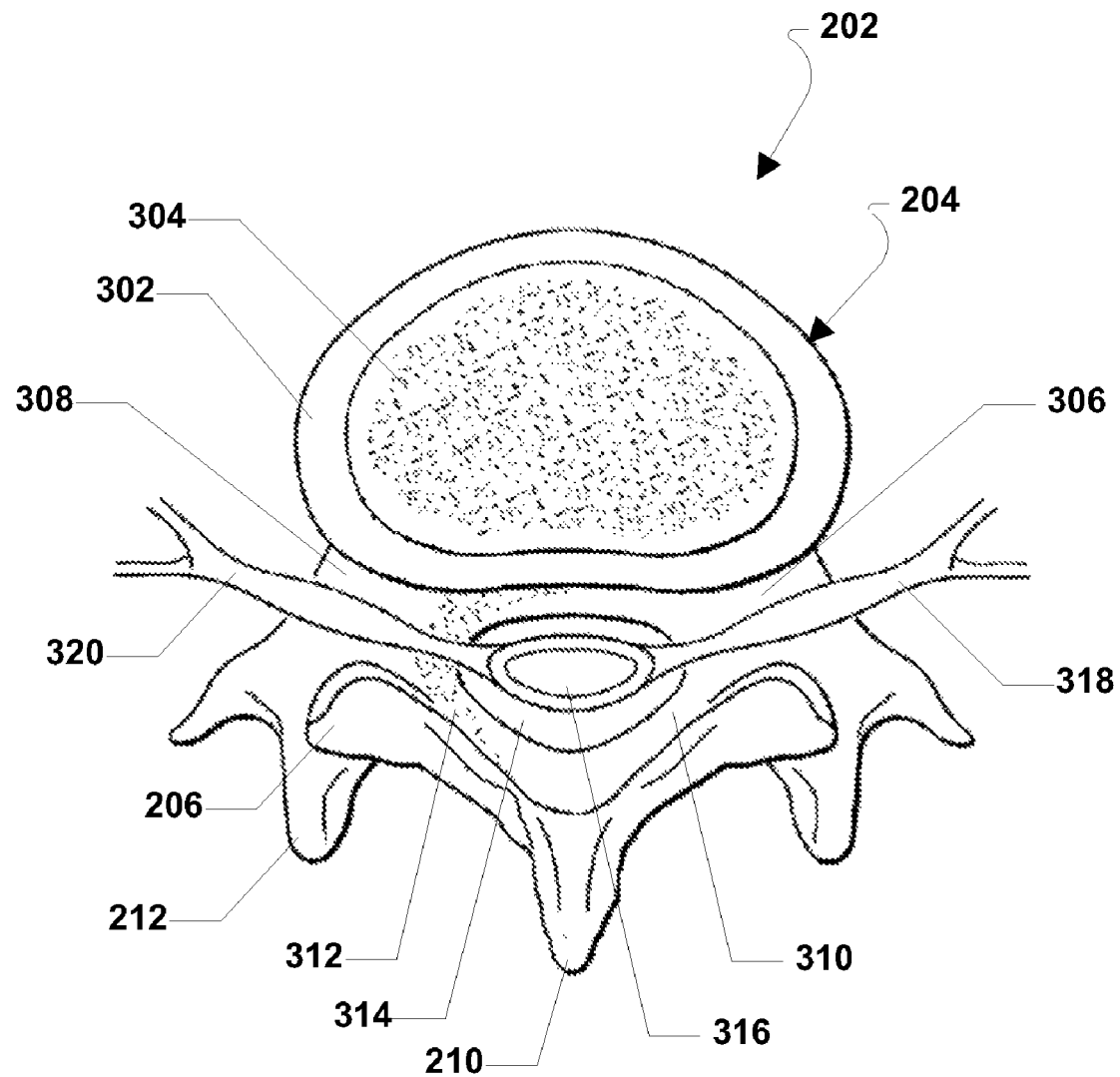
FIG. 3 includes a top plan view illustration of a vertebra.

Referring to FIG. 3, a vertebra, e.g., the inferior vertebra 202 (FIG. 2), is illustrated. As illustrated, the vertebral body 204 of the inferior vertebra 202 includes a cortical rim 302 composed of cortical bone. Also, the vertebral body 204 includes cancellous bone 304 within the cortical rim 302. The cortical rim 302 is often referred to as the apophyseal rim or apophyseal ring. Further, the cancellous bone 304 is softer than the cortical bone of the cortical rim 302.

As illustrated in FIG. 3, the inferior vertebra 202 further includes a first pedicle 306, a second pedicle 308, a first lamina 310, and a second lamina 312. Further, a vertebral foramen 314 is established within the inferior vertebra 202. A spinal cord 316 passes through the vertebral foramen 314. Moreover, a first nerve root 318 and a second nerve root 320 extend from the spinal cord 316.

The vertebrae that make up the vertebral column have slightly different appearances as they range from the cervical region to the lumbar region of the vertebral column. However, all of the vertebrae, except the first and second cervical vertebrae, have the same basic structures, e.g., those structures described above in conjunction with FIG. 2 and FIG. 3. The first and second cervical vertebrae are structurally different than the rest of the vertebrae in order to support a skull.

Description of a Percutaneous Surgical Assembly

In a particular embodiment, a percutaneous surgical assembly includes a subcutaneous screw coupled to a percutaneous rod. The percutaneous rod includes an axial lumen, which permits a set screw to be inserted therethrough and coupled with the subcutaneous screw. The percutaneous rod may also be used to adjust the position of a vertebra, in particular, relative to other vertebra of a patient's spine. When in use, the subcutaneous screw may engage a hard tissue structure, such as an osteal structure, and the percutaneous rod may extend from a head of the subcutaneous screw through soft tissue including the dermal layers. In particular, the subcutaneous screws may be accessed percutaneously with the use of a percutaneous rod coupled to the subcutaneous screw. The percutaneous rod may permit the subcutaneous screw to be accessed through small incisions and may permit a tether to be inserted into channels in the subcutaneous screws substantially parallel with an axis of the spine. Further, the percutaneous rob may permit set screws to be inserted into the subcutaneous screws percutaneously without a large incision site.

Figure 4:
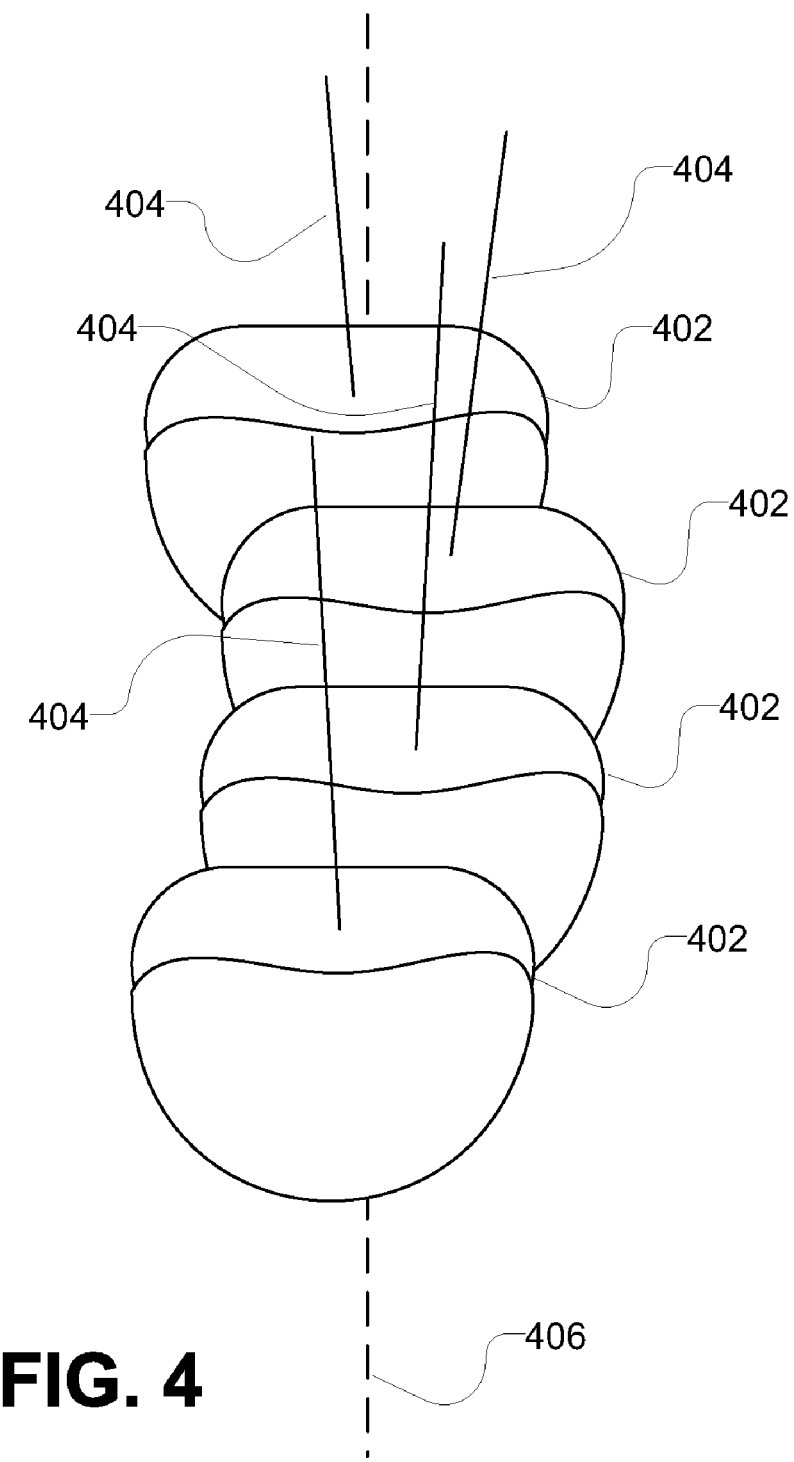
FIG. 4, FIG. 5, and FIG. 6 include illustrations of exemplary spinal positioning systems.
Figure 5:
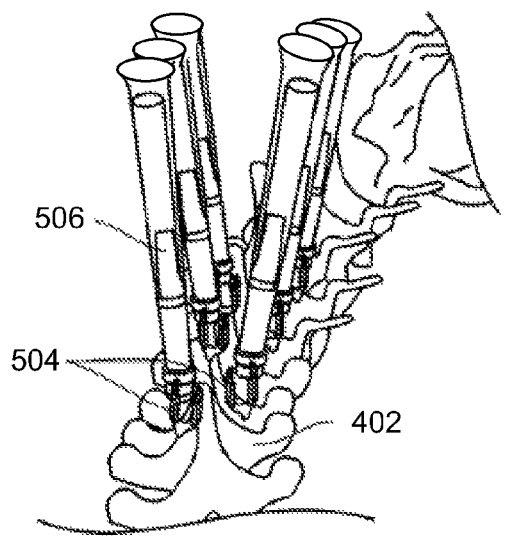
Figure 6:
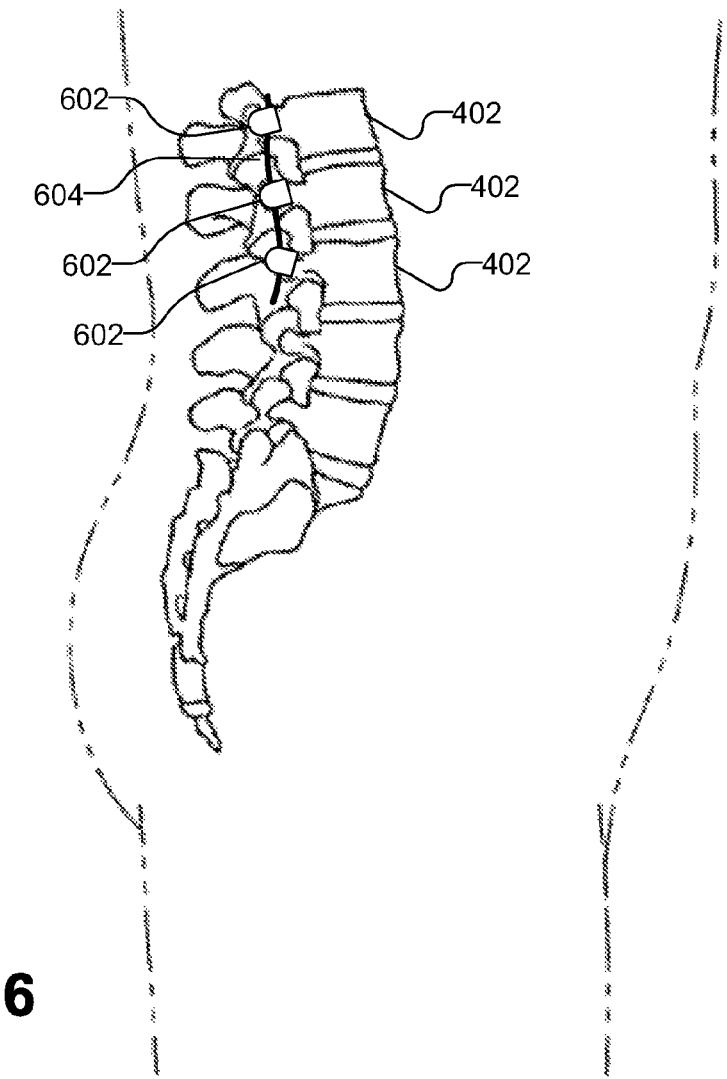

As illustrated in FIG. 4, FIG. 5, and FIG. 6, the subcutaneous screw may engage vertebrae 402. FIG. 4 includes an illustration of a set of conceptual vertebrae 402 that are out of alignment. A set of subcutaneous screws may be coupled to the vertebrae and a set of percutaneous rods may be coupled to the set of subcutaneous screws to form a leveraging system 404. The vertebrae may be aligned or positioned using the leveraging system.

As illustrated in FIG. 5, the subcutaneous screw may be a pedicle screw 504. For example, the pedicle screw 504 is inserted into at least one pedicle of the vertebra 403. A percutaneous rod 506 is coupled to the pedicle screw 504. In a particular example, the percutaneous rod 506 includes an axial lumen through which the pedicle screw 504 may be accessed. For example, a set screw may be coupled with pedicle screw 504. Further, the percutaneous rod 506 may be used to position vertebrae relative to each other. In particular, the pedicle screw 504 may include a channel in alignment with an axis of the spine and the percutaneous rod 506 may allow access to the channel. As view in cross-section in FIG. 6, the pedicle screws 602 are inserted into the pedicles of the vertebrae 402. A tether 604 is tensioned between and secured to the heads of the pedicle screws 602. For example, the tether 604 may be threaded through channels of the pedicle screws 504 and a set screw may be applied to engagement structures of the pedicle screw 504 via percutaneous rod 506 to secure the tether to the channel. As a result, the relative movement of the vertebrae 402 are limited at least in the axial direction in line with the tether.

The tether is an elongated member that resists elongation in a direction along its axis and is flexible otherwise. In an example, the tether includes an elastomeric member, woven fibers, a drawn fiber, or a combination thereof. For example, the elastomeric member may be formed of a diene elastomer, such as ethylene propylene diene monomer (EPDM) elastomer or ethylene-propylene rubber (EPR), a silicone elastomer, or a combination thereof. In particular, the fibers may be formed of strong polymeric materials, such as polyaramide, polyolefin, polyester, polyether, polyimide, a phenyl-based polymer, or a combination thereof. Further, the polyolefin material can include polypropylene, polyethylene, halogenated polyolefin, flouropolyolefin, or a combination thereof. The polyether materials can include polyetherketone (PEK), polyetheretherketone (PEEK), polyetherketoneketone (PEKK), polyetherketoneetherketoneketone (PEKEKK), or a combination thereof. Particular rigid-rod polymers can include copolymers that, in addition, to a phenylene group, include a benzoyl, an azole, a thiazole, an oxazol, a terephthalate group, or any combination thereof in the polymer chain. In a particular example, the rigid-rod polymer can include poly(phenylene benzobisthiazole) (PPBT), such as poly(p-phenylene benzobisthiazole). In another example, the rigid-rod polymer can include poly(phenylene benzobisoxazole) (PBO), such as poly(p-phenylene benzobisoxazole). In a further example, the rigid-rod polymer can include poly (phenylene benzimidazole) (PDIAB), such as poly(p-phenylene benzimidazole). In an additional example, the rigid-rod polymer can include poly(phenylene terephthalate) (PPTA), such as poly(p-phenylene terephthalate). In another example, the rigid-rod polymer can include poly(benzimidazole) (ABPBI), such as poly(2,5(6)benzimidazole). In a further example, the rigid-rod polymer can include poly(benzoyl-1,4-phenylene-co-1,3-phenylene). In addition, the rigid-rod polymer can include any combination of the above copolymers. A particular rigid-rod polymer can include a polymer sold under the trademark PARMAX®, available from Mississippi Polymer Technology, Inc. of Bay St. Louis, Miss.

Figure 7:
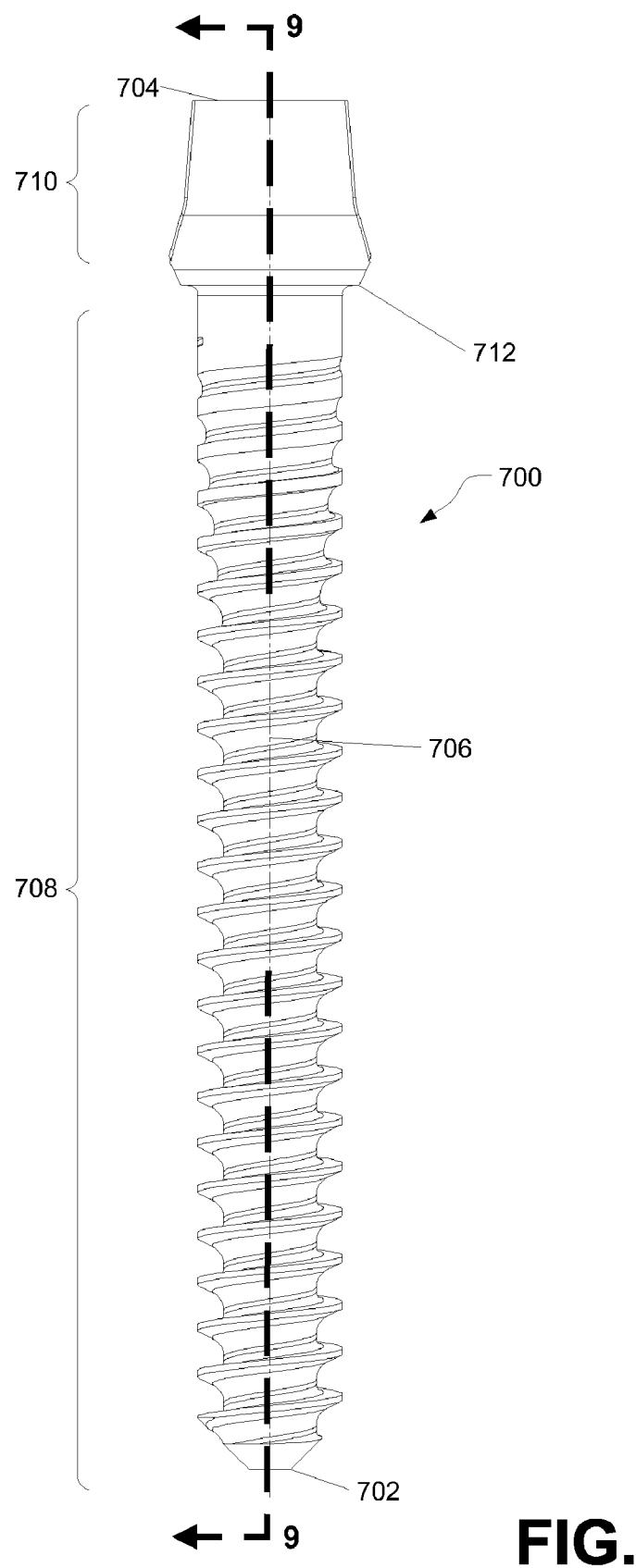
FIG. 7, FIG. 8, and FIG. 9 include illustrations of an exemplary subcutaneous screw.
Figure 8:
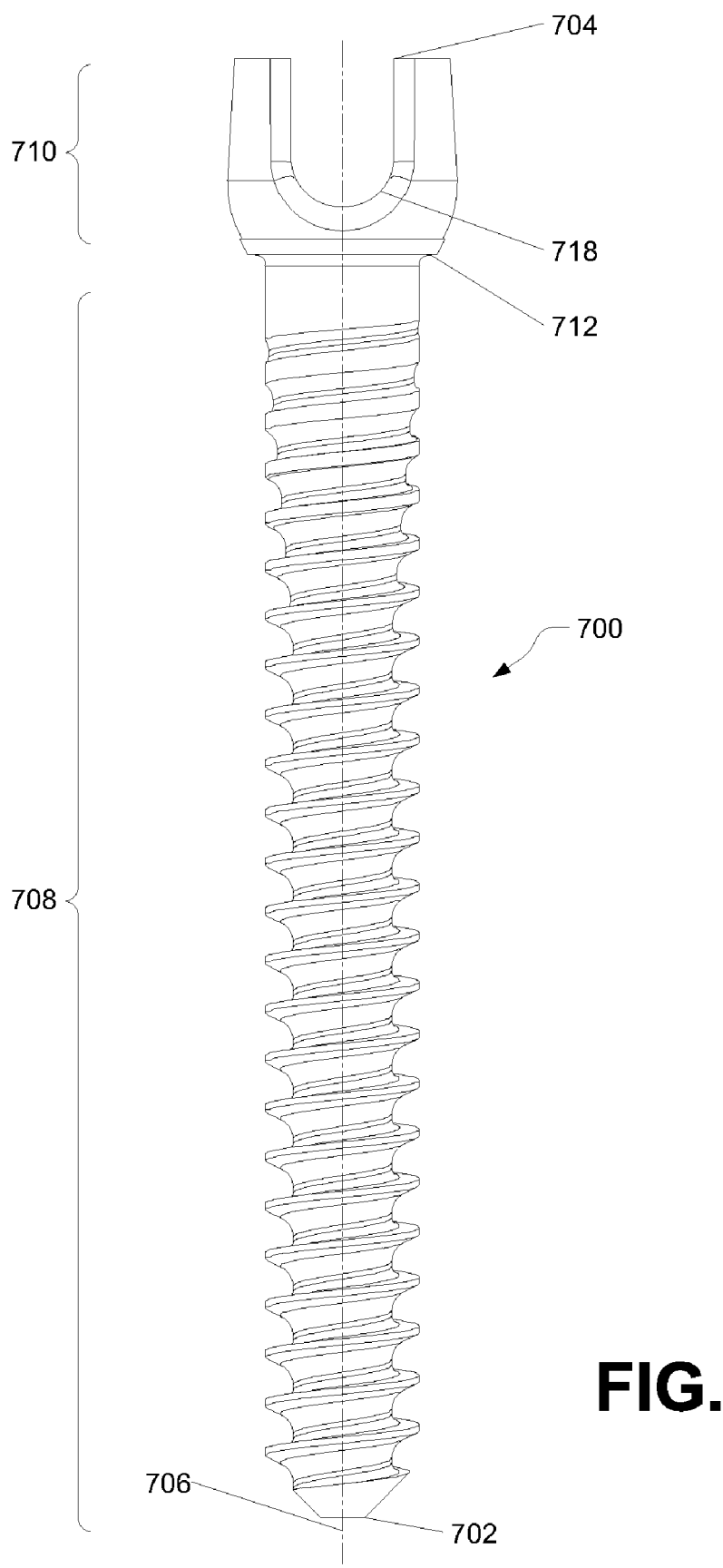
Figure 9:
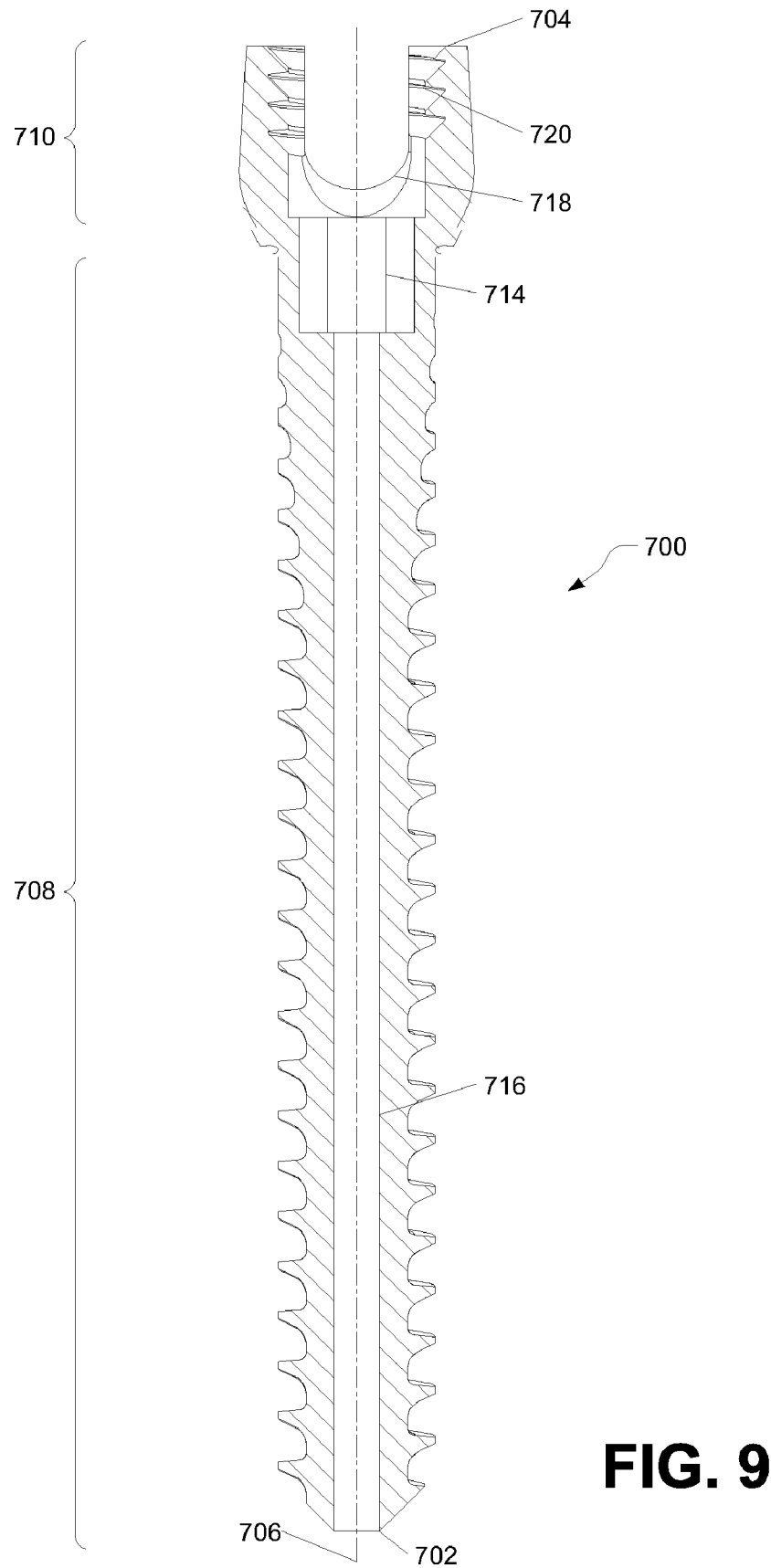

In an example, the tether is inserted into a channel formed in the head of a subcutaneous screw. FIG. 7, FIG. 8, and FIG. 9 illustrate an embodiment of a subcutaneous screw 700. In an exemplary embodiment, the subcutaneous screw is a pedicle screw. As illustrated in FIG. 7 and FIG. 8, the subcutaneous screw may include a proximal end 702, a distal end 704, and a major axis 706. The subcutaneous screw 700 may have a threaded shaft 708 and a head 710 attached to the threaded shaft 708. As illustrated, the head 710 is fixedly attached to the threaded shaft 708. Alternatively, the head 710 may be rotationally fixed to the threaded shaft 708, such as rotatable around one or more axis.

In addition, the head 702 may include a lip 712, for example, located proximally to where the head 710 is joined to the threaded shaft 708. In an example, the lip 712 may substantially prevent the subcutaneous screw 700 from being inserted too far into a bone.

As illustrated in FIG. 9, a tool engagement depression 714 may be formed within the subcutaneous screw 700. The tool engagement depression 714 may be formed partially in the threaded shaft 708 and the head 710 of the subcutaneous screw 700. The tool engagement depression 714 may be shaped to receive a tool for rotationally driving the subcutaneous screw 700 into an osteal structure, such as a pedicle of a vertebral bone. In an example, the tool engagement depression 714 may have a hexagonal cross section to receive a hex bit.

Further, the threaded shaft 708 may include a central bore 716. In an embodiment, a probe or guidewire may extend through the central bore 716 of the subcutaneous screw 700. The guidewire may be used to guide the placement of the subcutaneous screw 700 and may be used to influence both position and orientation of the subcutaneous screw 700. In particular, the guidewire may be used to guide the subcutaneous screw 700 to a position on a bone that has been tapped in preparation for insertion of the subcutaneous screw 700 and to assist in orienting the subcutaneous screw 700.

The head 710 of the subcutaneous screw 700 may include a channel 718 extending across the head 710 perpendicular to the axis 706 and an inner threaded lumen 720 extending coaxially with the central bore 716. The channel 718 and the inner threaded lumen 720 may intersect, as illustrated in FIG. 9. The channel 718 may be configured to receive an elongate fixing element, such as a rod, a wire, or a tether. The inner threaded portion 720 may be configured to receive a set screw. In an embodiment, the set screw may secure the elongate fixing element within the head 710 of the subcutaneous screw 700.

Figure 10:
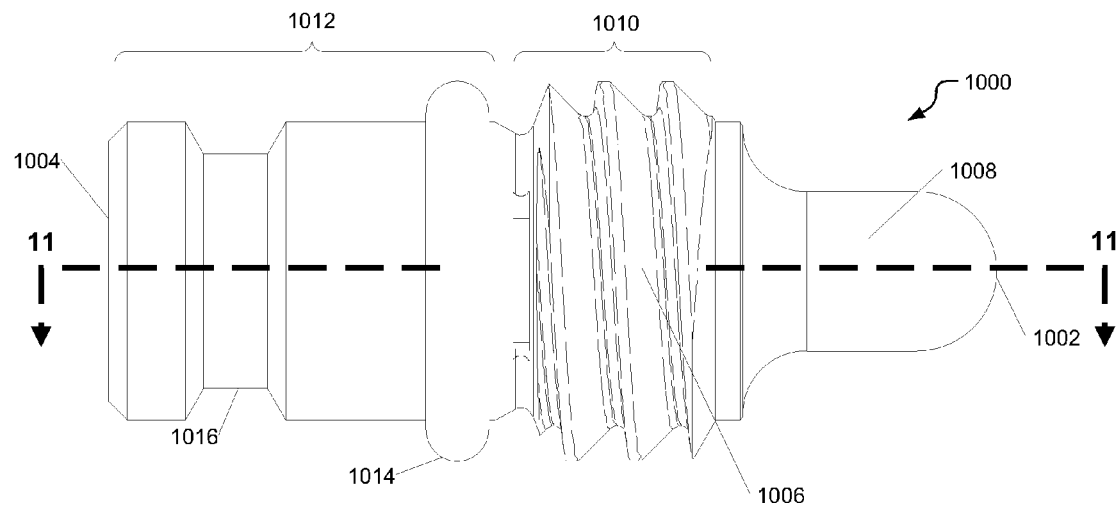
FIG. 10 and FIG. 11 include illustrations of exemplary set screws.
Figure 11:
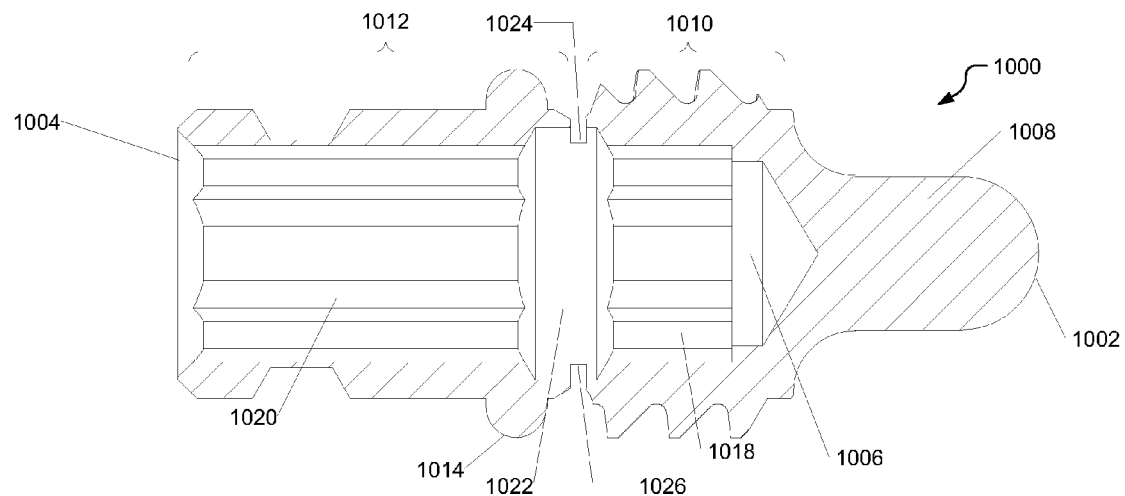

In addition to the subcutaneous screw 700, a percutaneous assembly may include a set screw to secure elements to the subcutaneous screw. Referring to FIG. 10 and FIG. 11, a set screw 1000 is illustrated. The set screw 1000 may be used to secure an elongate element within a head of a subcutaneous screw, such as subcutaneous screw 700. As illustrate in FIG. 10, the set screw 1000 has a proximal end 1002, a distal end 1004, and a major axis 1006. Starting from the proximal end 1002, the set screw 1000 includes a proximal projection 1008, a threaded portion 1010, and a breakaway head 1012. The proximal projection 1008 may secure an elongate fixing element within the head of the subcutaneous screw. The threaded portion 1010 may engage an inner threaded region of the subcutaneous screw to hold the set screw 1000 in place.

In an example, the breakaway head 1012 may be broken off the set screw 1000, leaving the threaded portion 1010 engaged with the inner threaded region of the subcutaneous screw. The breakaway head 1012 includes a flange 1014 to prevent the set screw 1000 from threading too deep into a head of a subcutaneous screw. Additionally, the breakaway head 1012 includes a channel 1016. For example, the channel 1016 may be used to retrieve the breakaway head 1012 from the head of the subcutaneous screw when the breakaway head 1012 has been detached from the set screw 1000.

FIG. 11 illustrates a cross-section of the set screw 1000 taken along line 11-11 of FIG. 10. Within the threaded portion 1010, the set screw 1000 may have a lower tool engagement channel 1018. An upper tool engagement channel 1020 corresponding to the lower tool engagement channel 1018 may be formed within the breakaway head 1012. Between the breakaway head 1012 and the threaded portion 1010, a weakened region 1022 may be formed. Within the weakened region 1022, the wall of the set screw 1000 may be thinner to allow easier breakage for removal of the breakaway head 1012. Additionally, a first cut 1024 and a second cut 1026 located between the breakaway head 1012 and the threaded portion 1010 may further weaken the set screw 1000.

Description of Methods of Treating a Spine

In general, a tether is tensioned between subcutaneous screws coupled to osteal structures, such as the pedicles of adjacent vertebrae. In particular, a percutaneous system may be used to limit the size of the incisions used in performing the method. For example, percutaneous rod systems may be used to provide access to subcutaneous screws and guidewires, trocars, sheaths, cannulated rods, or combinations thereof can be used to guide tethers into channels of the subcutaneous screws.

Figure 12:
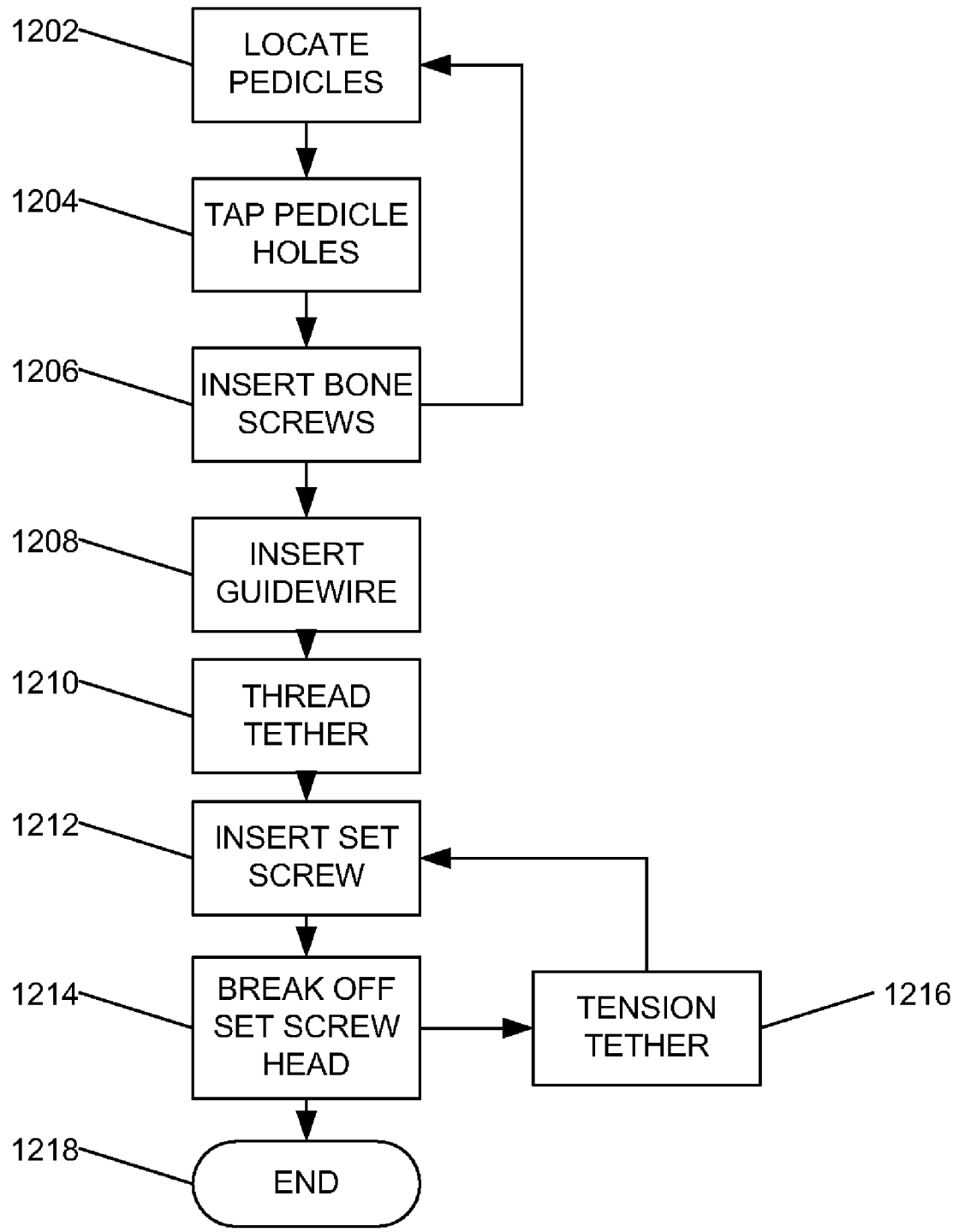
FIG. 12 includes a flow diagram illustrating an exemplary surgical method.

In an exemplary method illustrated in FIG. 12, a method of treating a spine includes locating a pedicle, as illustrated at 1202. The osteal structure may be located and relative positions determined through radiological techniques. An incision may be formed in the dermal layers proximal to the osteal structure of interest and a probe may be used to locate the pedicles. As illustrated at 1204, a hole or indentation may be formed in the pedicle. For example, a tap may be used to form the indentation.

As illustrated at 1206, a subcutaneous screw may be inserted into the hole in the pedicle and step illustrated at 1202 through 1206 may be repeated to insert multiple subcutaneous screws in a set of vertebrae. Optionally, a percutaneous rod may be coupled to each of the subcutaneous screws. In particular, the subcutaneous screw may have a threaded shaft and a head coupled to the threaded shaft. The head of the subcutaneous screw may have a channel for placement of a tether and an engagement structure to engage a set screw. The position of the head relative to the threaded shaft may be fixed or the head may be able to move relative to the threaded shaft, such as by rotating around one or more axis.

As illustrated at 1208, a guidewire may be inserted through the channel in the subcutaneous screw. In an exemplary embodiment, the guidewire may have a steerable tip. Alternatively, the tip may be shaped, such as an S-shape, a J-shape, or a bent shape. The steerable tip may be used to direct the guidewire through the channel in the subcutaneous screw. In particular, the guidewire may be directed to pass through channels of multiple subcutaneous screws and any tissue located between the subcutaneous screws.

Figure 13:
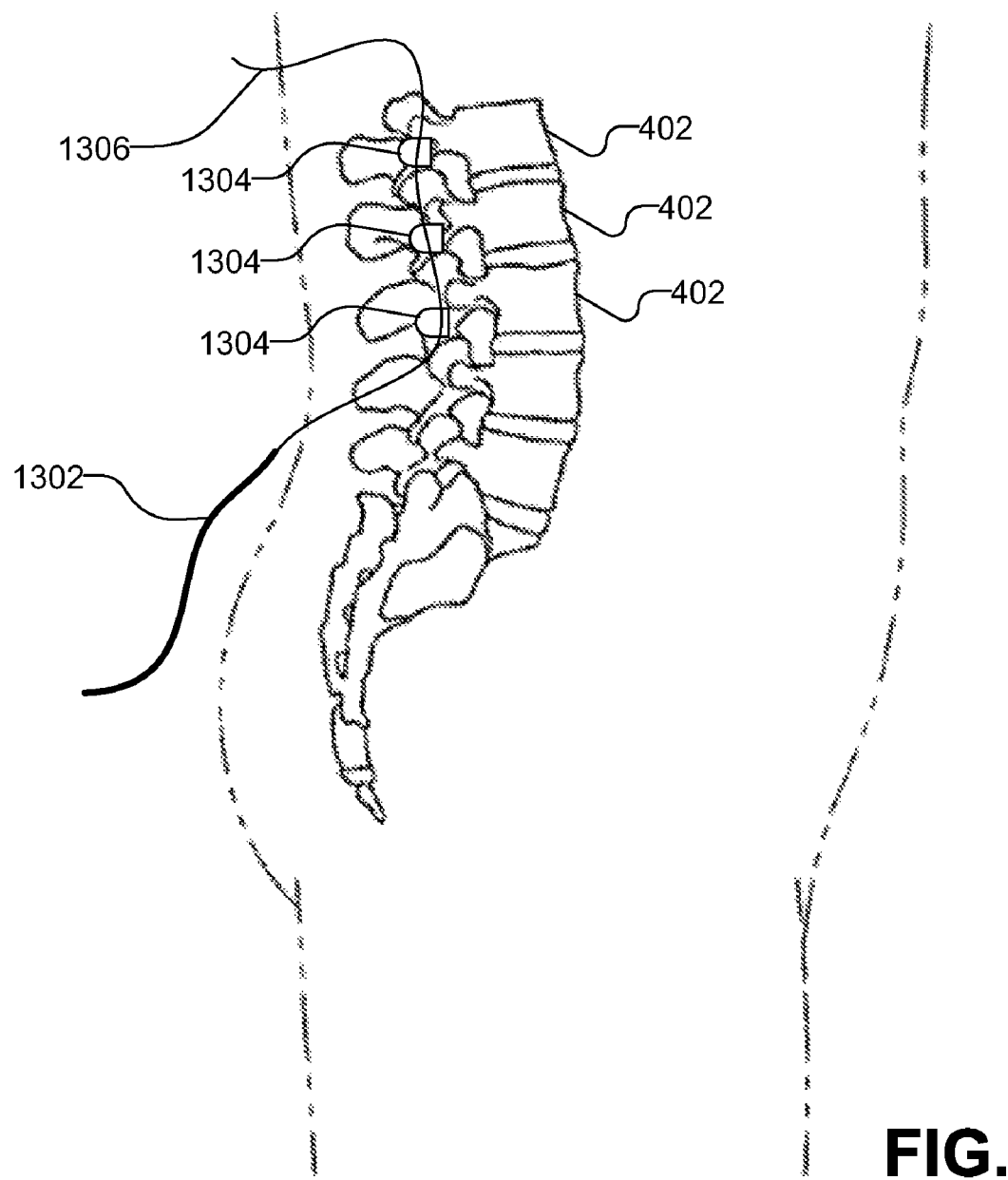
FIG. 13 includes an illustration of an exemplary surgical procedure.

As illustrated at 1210, a tether may be threaded through the channels. For example, as illustrated in FIG. 13, a tether 1302 may be attached to an end of the guidewire 1306 and drawn through the openings in the subcutaneous screws 1304.

As illustrated at 1212, a set screw may be inserted into the head of each subcutaneous screw to hold the tether within the head of the subcutaneous screw. The set screw may be tightened to prevent sliding of the tether or the set screw may be loose to allow the tether to slide through the head of the subcutaneous screw. In an exemplary embodiment, the tether may be allowed to slide through a subset of subcutaneous screws and may be prevented from sliding through another subset of subcutaneous screws. In an example, each of the set screws is set loosely within the subcutaneous screws prior to threading the tether to provide an additional guide.

As illustrated at 1214, a breakaway head of the set screw may be removed as each set screw is applied to secure the tether. Further, as illustrated at 1216, the tether may be tensioned. The tether may be tensioned to limit the relative motion between the vertebrae. The tether may be tensioned between setting each subcutaneous screw or the tether may be tensioned once. In particular, a first set screw may be applied, the breakaway end removed, and tension may be applied to the tether. Subsequently, a second set screw may be applied, the breakaway end removed, and additional tension may be applied to the tether. Further, a third set screw may be applied to a third subcutaneous screw. Optionally, the first set screw may be tightly applied to prevent movement of the tether relative to the first subcutaneous screw, the second and third set screws may be loosely applied to permit movement of tether prior to tensioning the tether, the tether may be tensioned, and the second and third set screws tightened to prevent further movement.

The method may end, as illustrated at 1218. For example, the surgical site may be closed, such as through suturing soft tissues.

Figure 14:
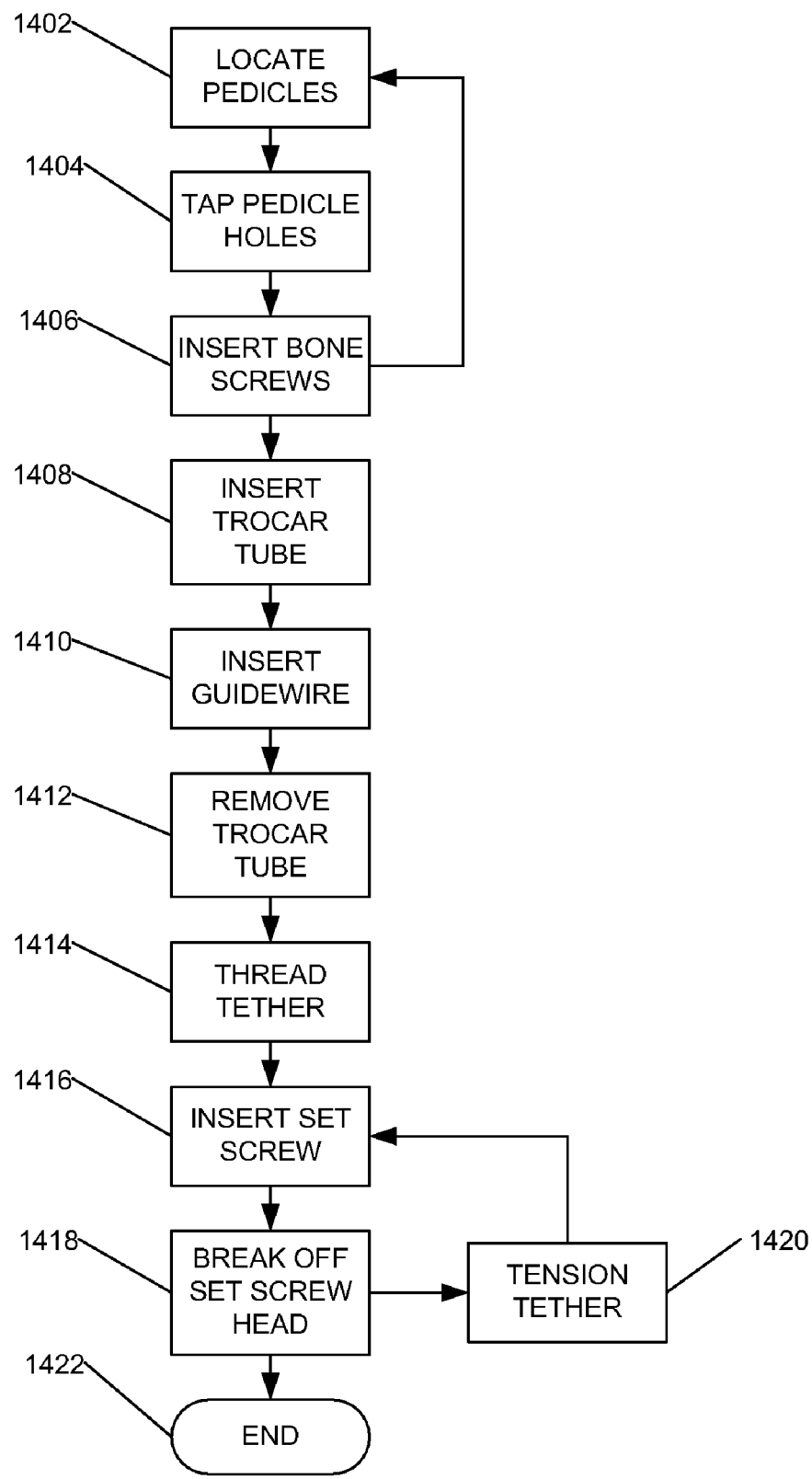
FIG. 14 and FIG. 15 include flow diagrams illustrating exemplary surgical methods.

In an additional method illustrated in FIG. 14, a method of treating a spine includes locating a pedicle, as illustrated at 1402. As above, the osteal structure may be located and relative positions determined through radiological techniques. An incision may be formed in the dermal layers proximal to the osteal structure of interest and a probe may be used to locate the pedicles. As illustrated at 1404, a hole or indentation may be formed in the pedicle. For example, a tap may be used to form the indentation.

As illustrated at 1406, a subcutaneous screw may be inserted into the indentation in the pedicle. The subcutaneous screw may have a threaded shaft and a head coupled to the threaded shaft. The head of the subcutaneous screw may have a channel for placement of a tether and an engagement structure to engage a set screw. Further, steps illustrated at 1402 through 1406 may be repeated to insert multiple subcutaneous screws in a set of vertebrae. Optionally, a percutaneous rod may be coupled to each of the subcutaneous screws.

As illustrated at 1408, a trocar tube may be inserted through the channel in the heads of the subcutaneous screws and any tissue located between the subcutaneous screws. For example, the trocar tube may include a handle and may be guided through the channels of the subcutaneous screws. As illustrated at 1410, a guidewire may be inserted through the tube, and, as illustrated at 1412, the trocar tube may be removed leaving the guidewire in place.

A tether may be threaded through the channels in the subcutaneous screws, as illustrated at 1414. For example, the tether may be attached to an end of the guidewire and drawn through the channels in the subcutaneous screws.

As illustrated at 1416, a set screw may be inserted into the head of the subcutaneous screw to hold the tether within the head of the subcutaneous screw. The set screw may be tightened to prevent sliding of the tether or the set screw may be loose to allow the tether to slide through the head of the subcutaneous screw. In an exemplary embodiment, the tether may be allowed to slide through a subset of subcutaneous screws and be prevented from sliding through another subset of subcutaneous screws. In an example, each of the set screws is set loosely within the subcutaneous screws prior to threading the tether to provide an additional guide. As illustrated at 1418, the breakaway head of the set screw may be removed upon securing the tether at each screw.

Further, as illustrated at 1420, the tether may be tensioned. The tether may be tensioned to limit the relative motion between the vertebrae. The tether may be tensioned between setting each subcutaneous screw or the tether may be tensioned once. In particular, a first set screw may be applied, the breakaway end removed, and tension may be applied to the tether. Subsequently, a second set screw may be applied, the breakaway end removed, and additional tension may be applied to the tether. Further, a third subcutaneous screw may be applied. Optionally, the first set screw may be tightly applied to prevent movement of the tether relative to the first subcutaneous screw, the second and third set screws may be loosely applied to permit movement of tether prior to tensioning the tether, the tether may be tensioned, and the second and third set screws tightened to prevent further movement.

The method may end, as illustrated at 1422, and the surgical site closed.

Figure 15:
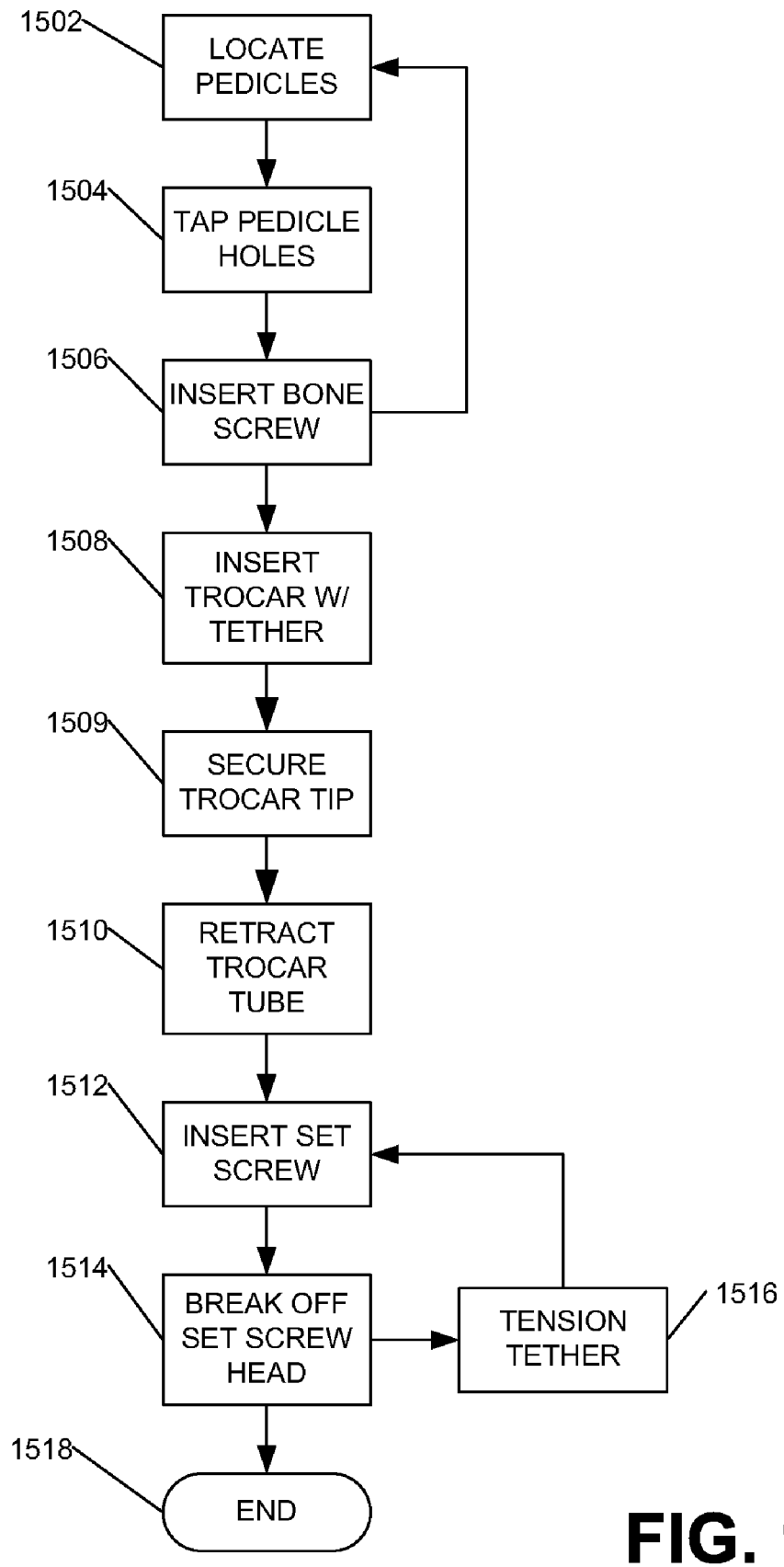

In a further embodiment, a method of treating a spine is illustrated in FIG. 15. As illustrated at 1502, a pedicle may be located, and, as illustrated at 1504, a hole or indentation may be formed in the pedicle. For example, a tap may be used to form the indentation.

As illustrated at 1506, a subcutaneous screw may be inserted into the indentation in the pedicle. The subcutaneous screw may have a threaded shaft and a head coupled to the threaded shaft. The head of the subcutaneous screw may have a channel for placement of a tether and an engagement structure to engage a set screw. As above, the steps illustrated at 1502 through 1506 may be repeated to insert multiple subcutaneous screws in a set of vertebrae. Optionally, a percutaneous rod may be coupled to each of the subcutaneous screws.

Figure 16:
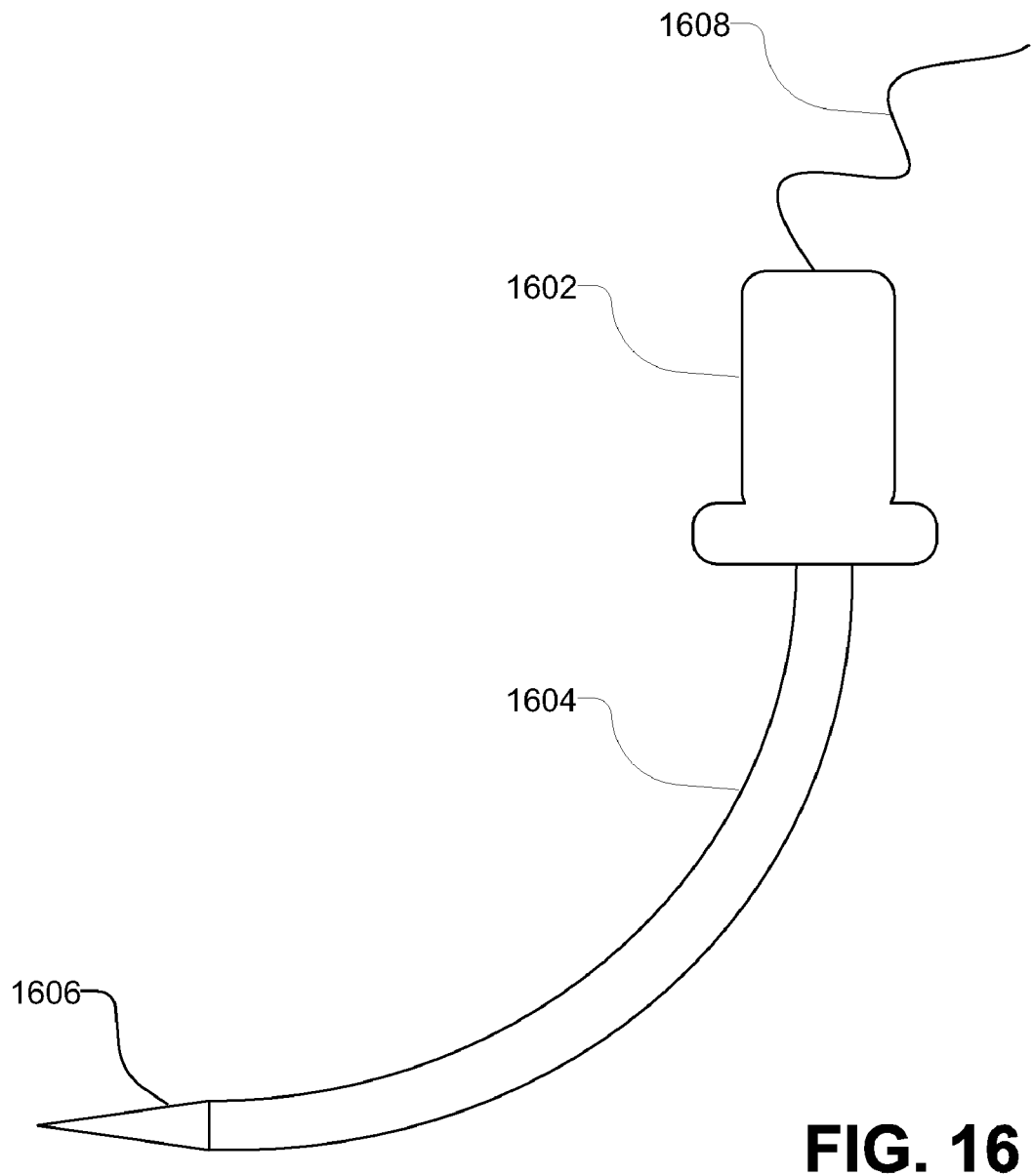
FIG. 16 includes an illustration of an exemplary trocar system.

As illustrated at 1508, a trocar tube and tether may be inserted through the channels in the head of the subcutaneous screws and through any tissue located between the subcutaneous screws. The tether may be located inside the trocar tube. In particular, the trocar may include a separable tip and the tether may be secured to the separable tip. For example, as illustrated in FIG. 16, a trocar may include an elongated member 1604 and a handle 1602. A lumen may extend through the handle 1602 and the elongated member 1604. A tip 1606 may extend from an end of the elongated member 1604 opposite the handle 1602. In an example, the tip 1606 is separable from the elongated member 1604. In addition, the tip 1606 may be attached to a tether 1608 that extends from the tip 1606 through the lumen of the elongated member 1604 and out of an end of the handle 1602. In particular, the tip 1606 or the tether 1608 near the tip 1606 may be secured in a first of the subcutaneous screws, as illustrated at 1509. As illustrated at 1510, the trocar tube may be removed leaving the tether in place. Alternatively, the tip 1606 may be secured with a tool and the trocar tube removed.

As illustrated at 1512, a set screw may be inserted into the head of the subcutaneous screw to secure the tether within the head of the subcutaneous screw. The set screw may prevent sliding of the tether or the set screw may be loose to allow the tether to slide through the head of the subcutaneous screw. As illustrated at 1514, a breakaway head of the set screw may be removed, and as illustrated at 1516, the tether may be tensioned. The tether may be tensioned to limit the relative motion between the vertebrae. In particular, a set screw may be applied, the breakaway end removed, and tension may be applied to the tether. Subsequently, another set screw may be applied, the breakaway end removed, and additional tension may be applied to the tether. Further, a third subcutaneous screw may be applied. Optionally, the first set screw may be tightly applied to prevent movement of the tether relative to the first subcutaneous screw, the second and third set screws may be loosely applied to permit movement of tether prior to tensioning the tether, the tether may be tensioned, and the second and third set screws tightened to prevent further movement. The method may end, as illustrated at 1518.

Figure 17:
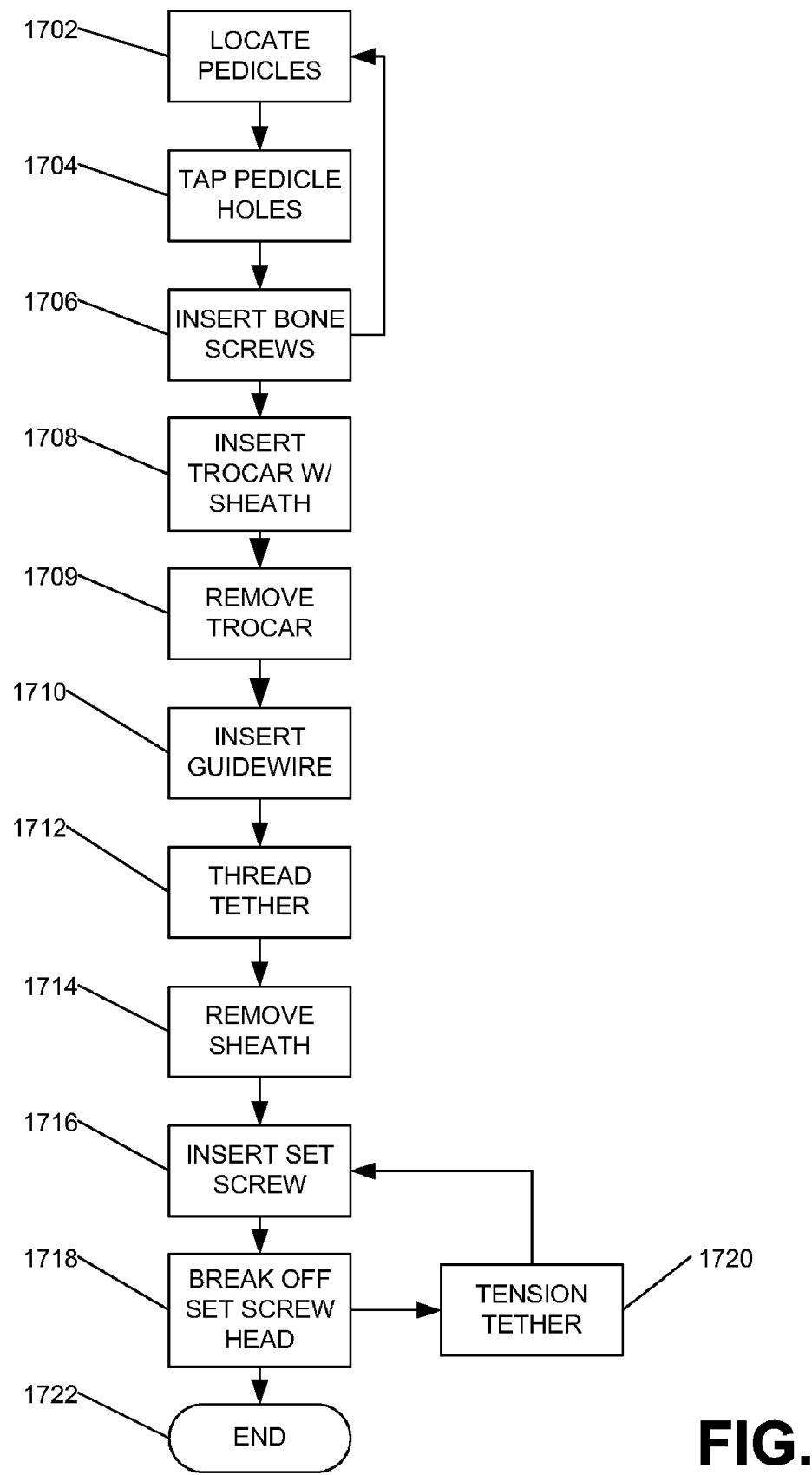
FIG. 17 and FIG. 18 include flow diagrams illustrating exemplary surgical methods.

In an additional embodiment, a method of treating a spine is illustrated at FIG. 17. As illustrated at 1702, a pedicle may be located, and as illustrated at 1704, an indentation may be formed in the pedicle. As illustrated at 1706, a subcutaneous screw may be inserted into the indentation in the pedicle. The subcutaneous screw may have a threaded shaft and a head coupled to the threaded shaft. The head of the subcutaneous screw may have a channel for placement of a tether and an engagement structure to engage a set screw. In particular, steps illustrated at 1702 through 1706 may be repeated to insert multiple subcutaneous screws in a set of vertebrae. Optionally, a percutaneous rod may be coupled to each of the subcutaneous screws.

As illustrated at 1708, a trocar with a sheath may be inserted through the channels in the head of the subcutaneous screws. In an example, the sheath may be a polymeric tube surrounding the trocar. The trocar may be removed, as illustrated at 1709, and a guidewire may be guided through the sheath, as illustrated at 1710. A tether may be coupled to the guidewire. As illustrated at 1712, a tether may be inserted through the sheath. For example, the guidewire may be threaded through the sheath and a tether attached to the guidewire may be drawn through the sheath. As illustrated at 1714, the sheath may be removed leaving the tether in place.

As above, a set screw may be inserted into the head of the subcutaneous screw to hold the tether within the head of the subcutaneous screw, as illustrated at 1716, and the set screw head may be broken away, as illustrated at 1718, after securing the tether in the particular subcutaneous screw. The set screw may prevent sliding of the tether or the set screw may be loose to allow the tether to slide through the head of the subcutaneous screw. In particular, the set screw may be tightly applied to an end of the tether prior to removing the sheath. In an exemplary embodiment, the tether may be allowed to slide through a subset of subcutaneous screws and be prevented from sliding through another subset of subcutaneous screws.

As illustrated at 1720, the tether may be tensioned. The tether maybe tensioned to limit the relative motion between the vertebrae. The tether may be tensioned between setting each subcutaneous screw or the tether may be tensioned once. In particular, a set screw may be applied, the breakaway end removed, and tension may be applied to the tether. Subsequently, a second set screw may be applied, the breakaway end removed, and additional tension may be applied to the tether. Further, a third subcutaneous screw may be applied. Optionally, the first set screw may be tightly applied to prevent movement of the tether relative to the first subcutaneous screw, the second and third set screws may be loosely applied to permit movement of tether prior to tensioning the tether, the tether may be tensioned, and the second and third set screws tightened to prevent further movement.

The method may end, as illustrated at 1722, with closing the surgical site.

Figure 18:
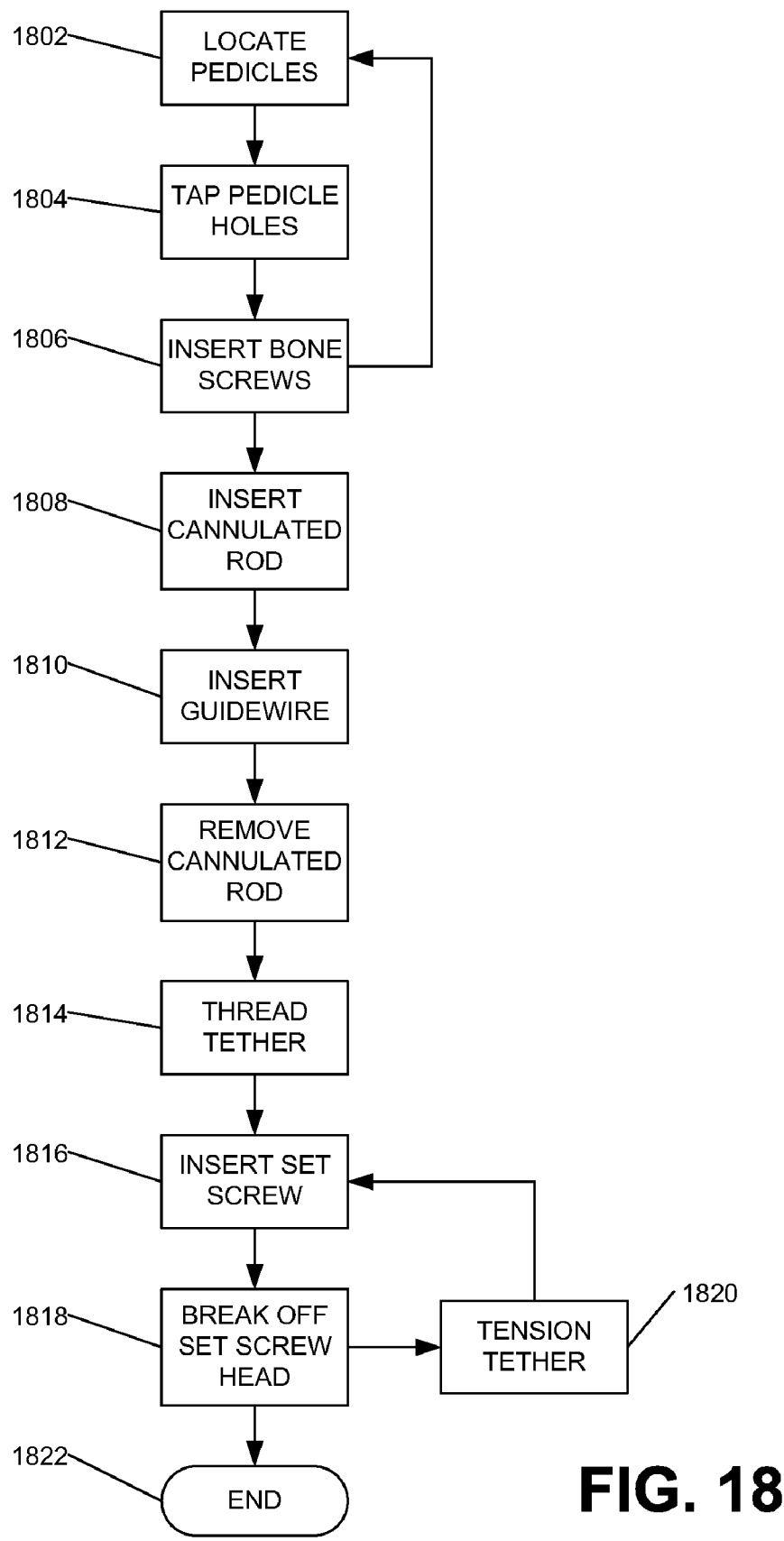

In a further embodiment, a method of treating a spine is illustrated at FIG. 18. As illustrated at 1802, a pedicle may be located, and, as illustrated at 1804, a hole or indentation may be formed in the pedicle. As illustrated at 1806, a subcutaneous screw may be inserted into the indentation in the pedicle. The subcutaneous screw may have a threaded shaft and a head coupled to the threaded shaft, and the head of the subcutaneous screw may have a channel for placement of a tether and an engagement structure to engage a set screw. In addition, the steps illustrated at 1802 through 1806 may be repeated to insert multiple subcutaneous screws in a set of vertebrae. Optionally, a percutaneous rod may be coupled to each of the subcutaneous screws.

Figure 19:
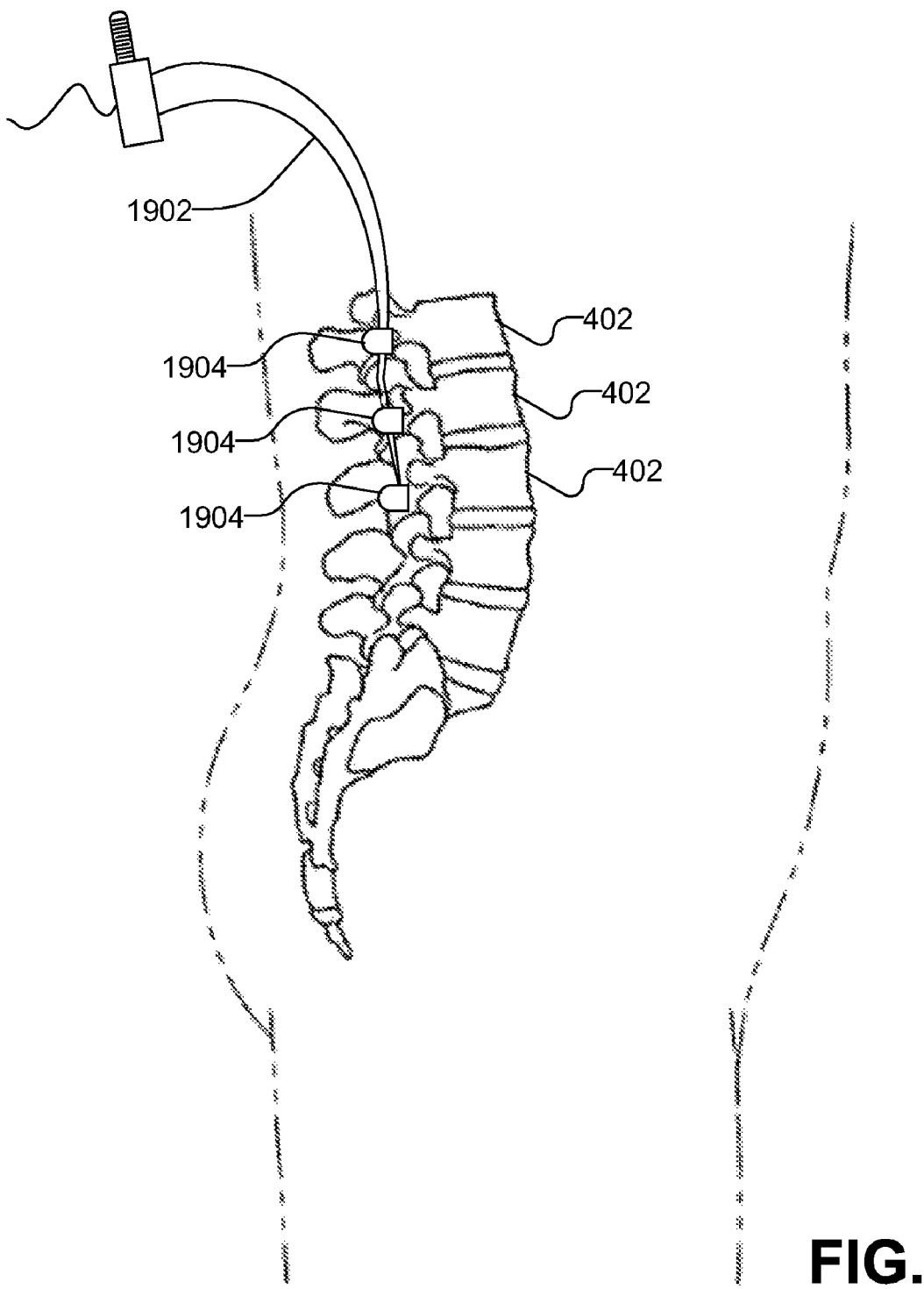
FIG. 19 includes an illustration of an exemplary surgical procedure.

As illustrated at 1808, a cannulated rod may be inserted through the channels in the subcutaneous screws, and, as illustrated at 1810, a guidewire may be inserted through the cannula within the cannulated rod. For example, FIG. 19 includes an illustration of a cannulated rod 1902 inserted through the heads of a set of subcutaneous screws 1904 that are coupled to vertebrae 402.

As illustrated at 1812, the cannulated rod may be withdrawn, leaving the guidewire in place. A tether may be inserted through the openings in the subcutaneous screws, as illustrated at 1814. For example, the tether may be attached to an end of the guidewire and the guidewire may be used to draw the tether through the openings in the subcutaneous screws.

As illustrated at 1816, a set screw may be inserted into the head of the subcutaneous screw to hold the tether within the head of the subcutaneous screw. In an example, each of the set screws is set loosely within the subcutaneous screws prior to threading the tether to provide an additional guide. As the tether is secured in each subcutaneous screw, the breakaway head of the set screw may be removed, as illustrated at 1818. Further, as illustrated at 1820, the tether may be tensioned. In particular, a set screw may be applied, the breakaway end removed, and tension may be applied to the tether. Subsequently, a second set screw may be applied, the breakaway end removed, and additional tension may be applied to the tether. Further, a third subcutaneous screw may be applied. Optionally, the first set screw may be tightly applied to prevent movement of the tether relative to the first subcutaneous screw, the second and third set screws may be loosely applied to permit movement of tether prior to tensioning the tether, the tether may be tensioned, and the second and third set screws tightened to prevent further movement. The method may end, as illustrated at 1822, with the closing of the surgical site.

Figure 20:
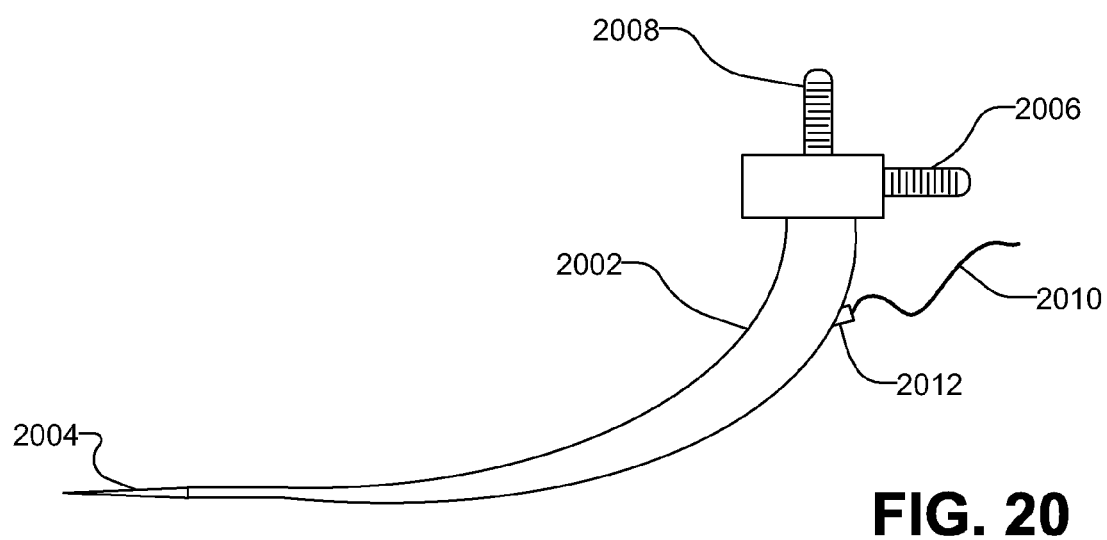
FIG. 20 includes an illustration of an exemplary cannulated device.

In an alternative embodiment, a cannulated rod may be used to insert the tether directly without use of a guidewire. In a particular example illustrated in FIG. 20, a cannulated rod 2002 may include a stearable tip 2004. For example, the cannulated rod 2002 may be steadied with the use of an attached handle 2006 extending from a proximal end and the stearable tip 2004 may be manipulated with a second handle 2008. In addition, the cannulated rod 2002 may include a port 2012 for receiving a tether 2010. In an example, the port 2012 is located on a backside or convex side of the curved cannulated rod 2002 below the handle 2006. Once the cannulated rod 2002 is guided into position in the channels of the subcutaneous screws, the tether may be guided through the tip 2004 and secured in a first subcutaneous screw. The cannulated rod 2002 may be removed, as described in relation to FIG. 18.

Description of a Surgical Kit

Figure 21:
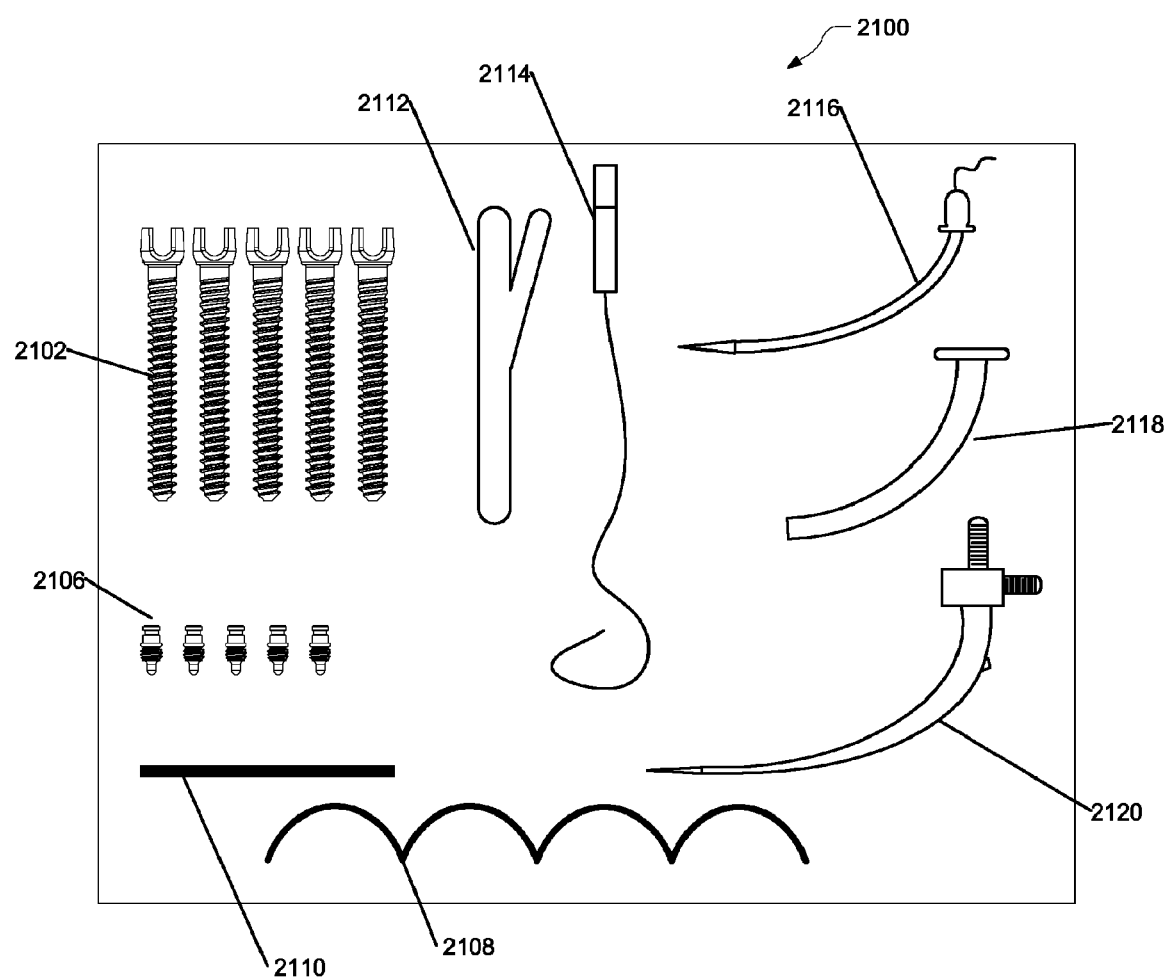
FIG. 21 includes an illustration of an exemplary surgical kit.

In a particular embodiment, elements of the percutaneous surgical assembly may be included in a surgical kit. Referring to FIG. 21, a kit 2100 is shown. The kit 2100 may include a plurality of subcutaneous screws 2102 and a plurality of set screws 2106. The subcutaneous screws 2102 may be similar to subcutaneous screw 700 and the set screws 2106 may be similar to set screw 1000. Additionally, the kit 2100 may include a tether 2108 and a needle 2110. Further, the kit 2100 may include a tensioning tool 2112. In a further example, the kit 2100 may optionally include a guidewire 2114, a trocar 2116, a sheath 2118, a cannulated rod 2120, or a combination thereof.

In general, one or more of the above elements may be stored in a sterilized package together. For example, the plurality of subcutaneous screws 2102 and the plurality of set screws 2106 may be housed within a sterilized package.

Conclusion

With the configuration of structure described above, fixing an elongated fixing element, such as a tether, to subcutaneous screws inserted into the vertebrae provides a method that may be used to treat a spine and substantially alleviate or minimize one or more symptoms associated with disc degeneration, facet joint degeneration, vertebral misalignment, or a combination thereof. For example, the tether may be installed between pedicles of adjacent vertebrae to maintain them at or near a predetermined distance therebetween.

In particular, embodiments of the above procedures permit use of small incisions in contrast to open spinal surgery. For example, percutaneous access to subcutaneous screws and the use of guidewires, trocars, sheaths, cannulated rods, or a combination thereof allows the use of small incision sites to access the vertebrae. Further, access to the spine can be achieve posterior in contrast to anterior. In addition, the set screws can be set loosely to provide an additional guide when treading the tether, such as when drawing the tether using a guidewire.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes may be made without departing from the scope of the invention as set forth in the claims below. Accordingly, the specification and figures are to be regarded in an illustrative rather than a restrictive sense, and all such modifications are intended to be included within the scope of invention.

As used herein, the terms "comprises," "comprising," "includes," "including," "has," "having" or any other variation thereof, are intended to cover a non-exclusive inclusion. For example, a process, method, article, or apparatus that comprises a list of features is not necessarily limited only to those features but may include other features not expressly listed or inherent to such process, method, article, or apparatus. Further, unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

Also, the use of "a" or "an" are employed to describe elements and components described herein. This is done merely for convenience and to give a general sense of the scope of the invention. This description should be read to include one or at least one and the singular also includes the plural unless it is obvious that it is meant otherwise.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

After reading the specification, skilled artisans will appreciated that certain features are, for clarity, described herein in the context of separate embodiments, may also be provided in combination in a single embodiment. Conversely, various features that are, for brevity, described in the context of a single embodiment, may also be provided separately or in any subcombination. Further, references to values stated in ranges include each and every value within that range.

What is claimed is:

1. A method of limiting relative movement of vertebrae, the method comprising:
   inserting a first pedicle screw into a first pedicle of a first vertebra, the first pedicle screw comprising a first U-shaped channel running perpendicular to a first central axis of the first pedicle screw defining a first concave bottom surface and a first engagement structure;
   inserting a second pedicle screw into a second pedicle of a second vertebra, the second pedicle screw comprising a second U-shaped channel running perpendicular to a second central axis of the second pedicle screw defining a second concave bottom surface and a second engagement structure;
   inserting a guidewire through the first and second channels;
   threading a tether attached to an end of the guidewire through the first and second U-shaped channels such that at least a portion of the tether engages the first and second concave bottom surfaces;
   inserting a first set screw to engage the first engagement structure and secure the tether to the first pedicle screw;
   applying tension to the tether; and
   inserting a second set screw to engage the second engagement structure and secure the tether to the second pedicle screw.

2. The method of claim 1, further comprising: inserting a third pedicle screw into a third pedicle of a third vertebra, the third pedicle screw comprising a third U-shaped channel running perpendicular to a third central axis of the third pedicle screw defining a third concave bottom surface and a third engagement structure.

3. The method of claim 2, wherein inserting the guidewire includes inserting the guidewire through the first, second, and third U-shaped channels.

4. The method of claim 2, wherein the method further comprising inserting a third set screw to engage the third engagement structure and secure the tether to the third pedicle screw prior to applying tension to the tether, the first set screw preventing movement of the tether, the second and third set screws permitting movement of the tether.

5. The method of claim 1, wherein inserting the first set screw comprises breaking a head of the first set screw.

6. The method of claim 1, further comprising making an incision in the dermal layer proximal to the first vertebra.

7. The method of claim 1, further comprising attaching a percutaneous rod to the first pedicle screw, the percutaneous rod providing access to the first engagement structure.

8. The method of claim 7, further comprising manipulating the percutaneous rod to manipulate the position of the first vertebra.

* * * * *